United States Patent [19]

Narula et al.

[11] Patent Number: 5,733,866
[45] Date of Patent: Mar. 31, 1998

[54] METHYL SUBSTITUTED HEXAHYDROINDANOLS AND ALKYL ETHERS THEREOF, ORGANOLEPTIC USES THEREOF, PROCESSES FOR PREPARING SAME AND PROCESS INTERMEDIATES THEREFOR

[75] Inventors: Anubhav P. S. Narula; James Joseph Koestler, both of Hazlet; Marie R. Hanna, Keyport, all of N.J.; Honorine Hattab, New York, N.Y.; Francis Charles Antoine Thibaudeau, Maisons Laffitte, France; Charles E. J. Beck, Summit, N.J.

[73] Assignee: International Flavors & Fragrances Inc., New York, N.Y.

[21] Appl. No.: 701,665

[22] Filed: Aug. 22, 1996

[51] Int. Cl.⁶ .................... A61K 7/46; C07F 3/00
[52] U.S. Cl. .................... 512/19; 556/135; 568/665; 568/819
[58] Field of Search ................ 556/135; 512/19; 568/819, 665

[56] References Cited

U.S. PATENT DOCUMENTS

| 3,681,464 | 8/1972 | Theimer, II | 260/586 R |
| 3,767,713 | 10/1973 | Theimer, I | 260/617 F |
| 4,535,192 | 8/1985 | Hall et al. | 568/819 |
| 4,902,672 | 2/1990 | Sprecker et al. | 512/19 |

*Primary Examiner*—Porfirio Nazario-Gonzalez
*Attorney, Agent, or Firm*—Arthur L. Liberman

[57] ABSTRACT

Described are methyl substituted hexahydroindanols and alkyl ethers thereof defined according to the generic structure:

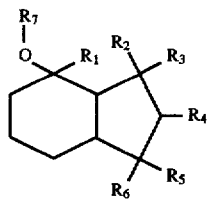

wherein $R_7$ represents hydrogen or $C_1$–$C_3$ alkyl; wherein $R_1$ represents methyl or ethyl; wherein $R_4$ represents methyl or hydrogen; and wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl and uses thereof in augmenting or enhancing the aroma of perfume compositions, colognes and perfumed articles including but not limited to perfumed polymers, solid or liquid anionic, cationic, nonionic or zwitterionic detergents, fabric softener compositions, fabric softener articles, cosmetic powders and hair preparations.

24 Claims, 23 Drawing Sheets

FIG.I
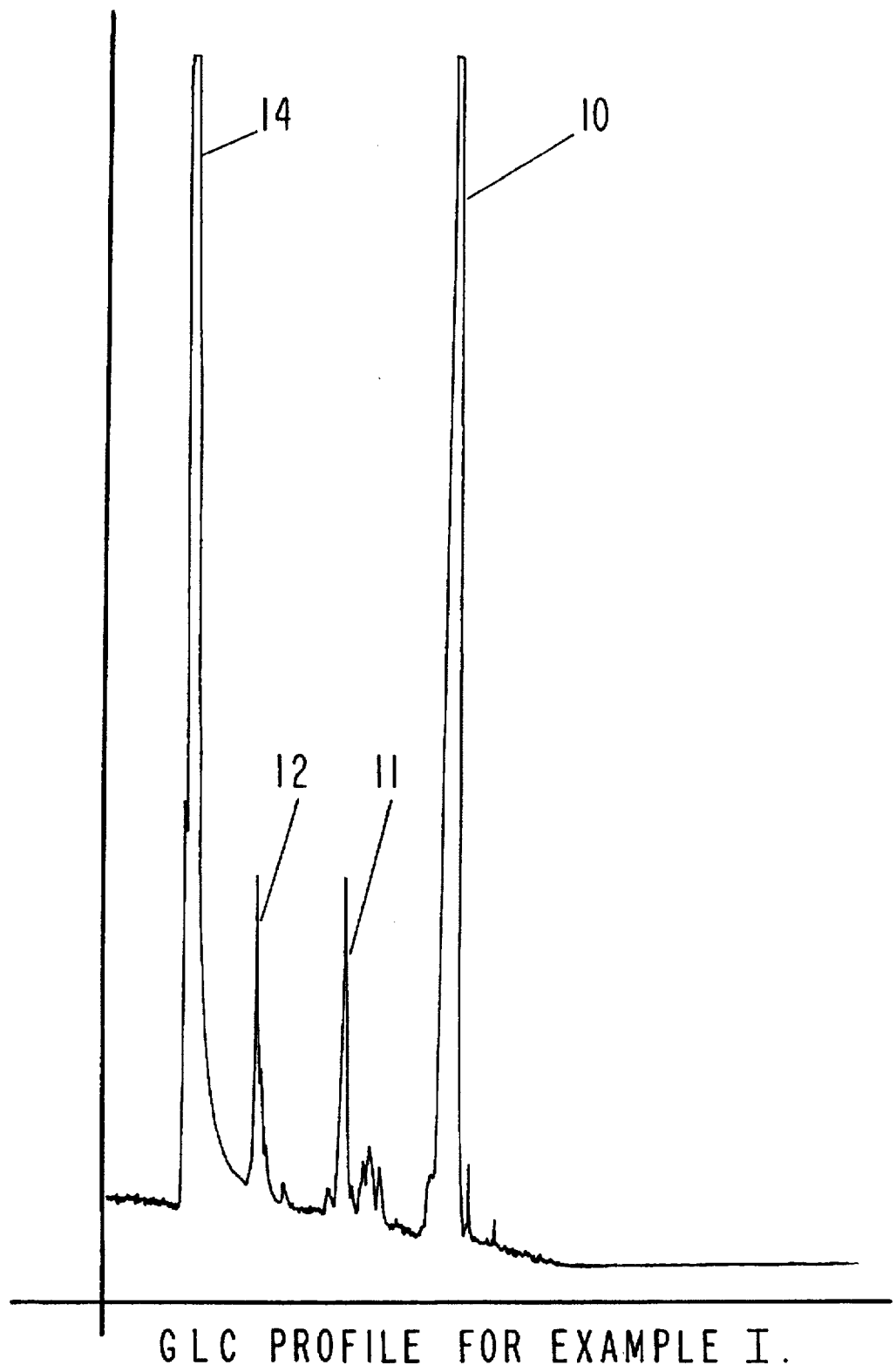
GLC PROFILE FOR EXAMPLE I.

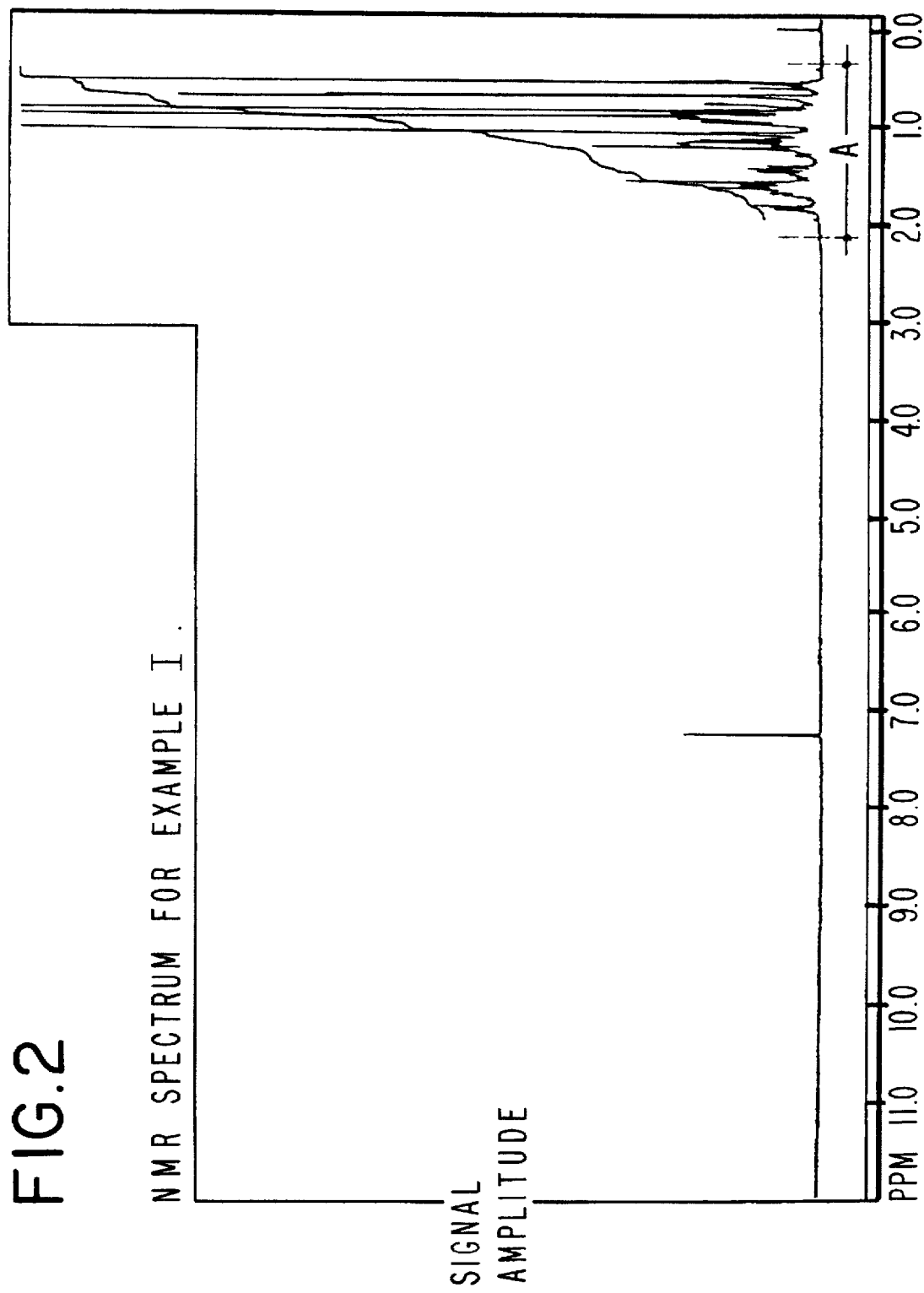

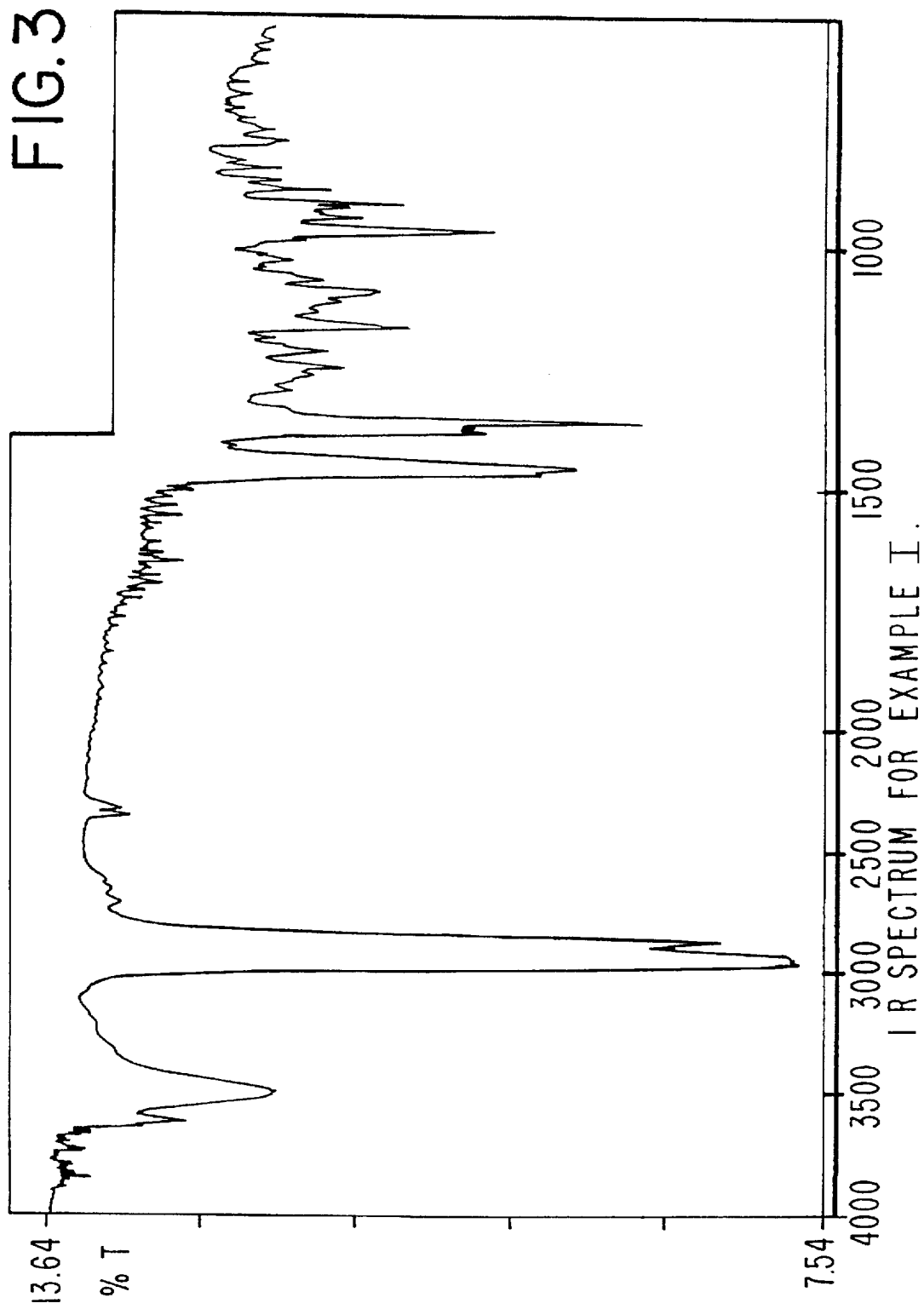

GLC PROFILE FOR EXAMPLE II.

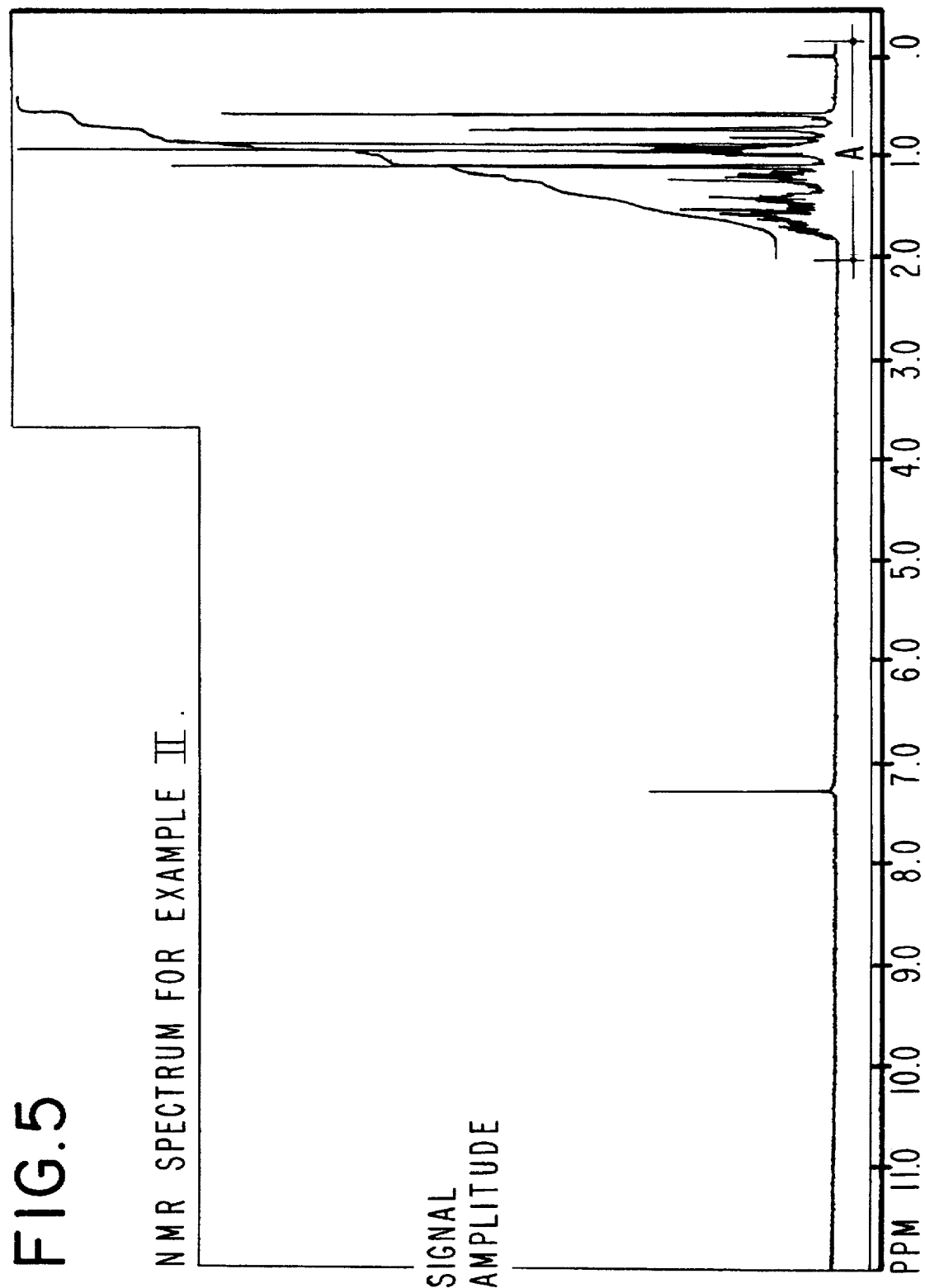
FIG.5 NMR SPECTRUM FOR EXAMPLE II.

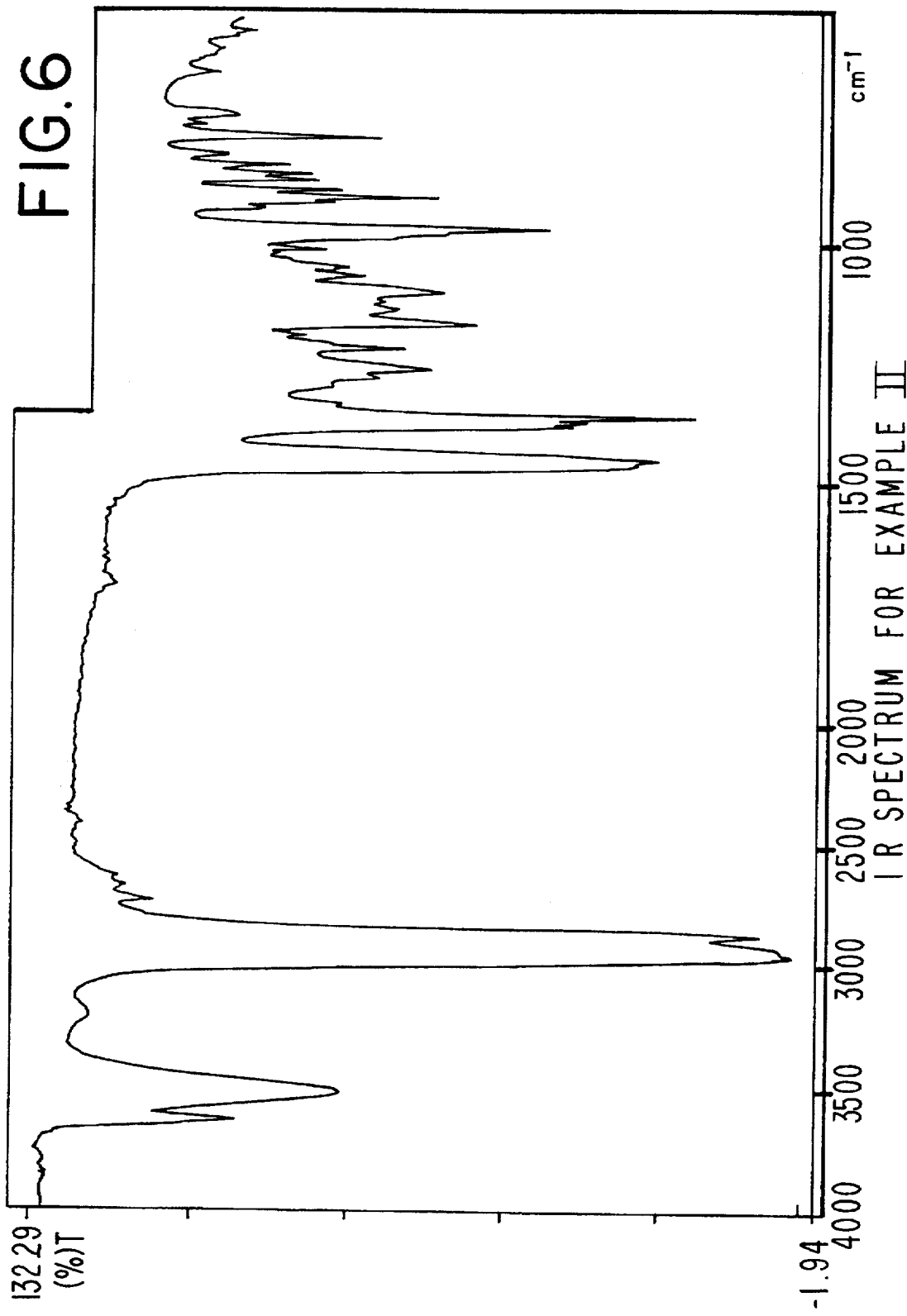

GLC PROFILE FOR EXAMPLE III.

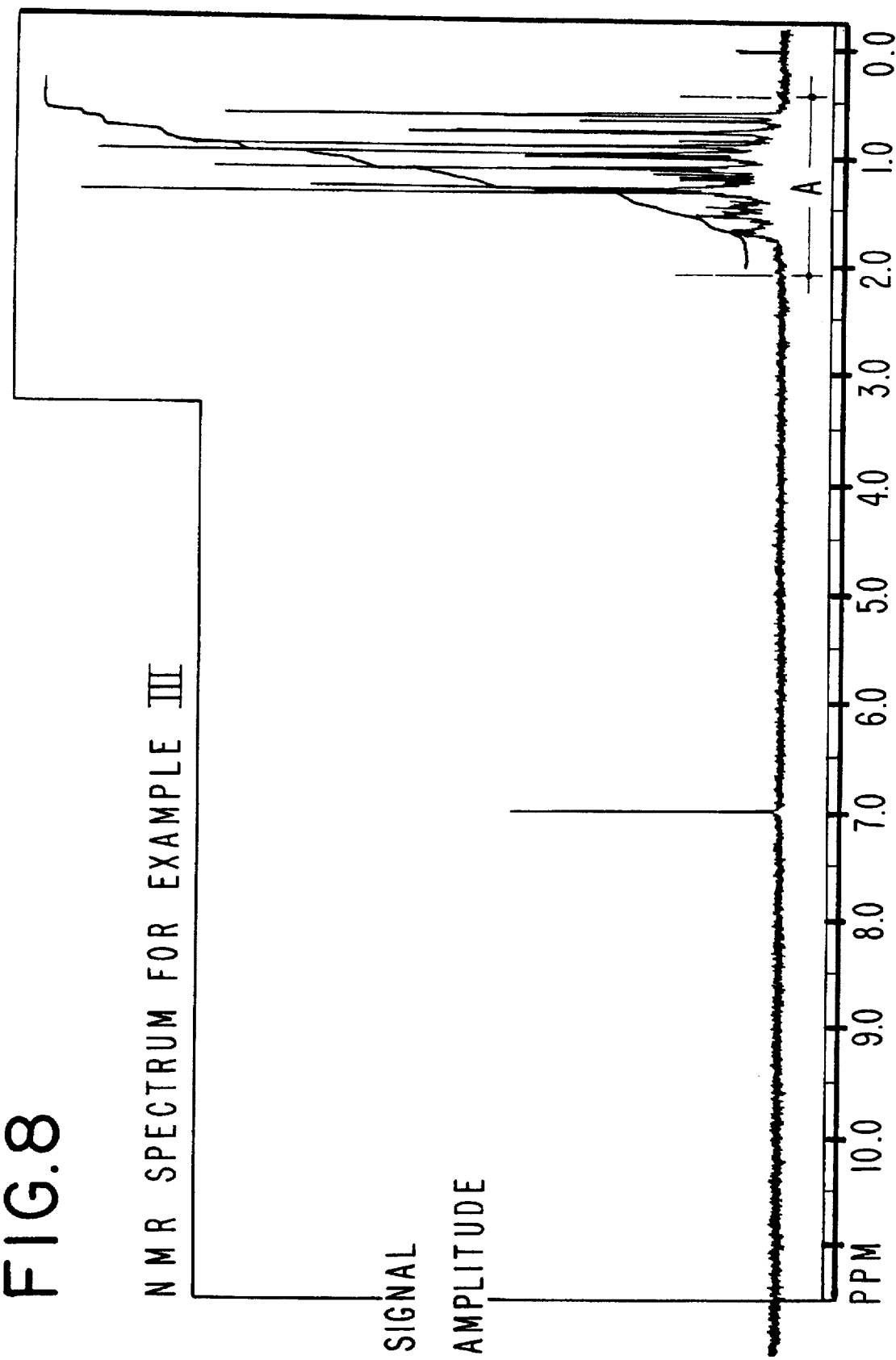

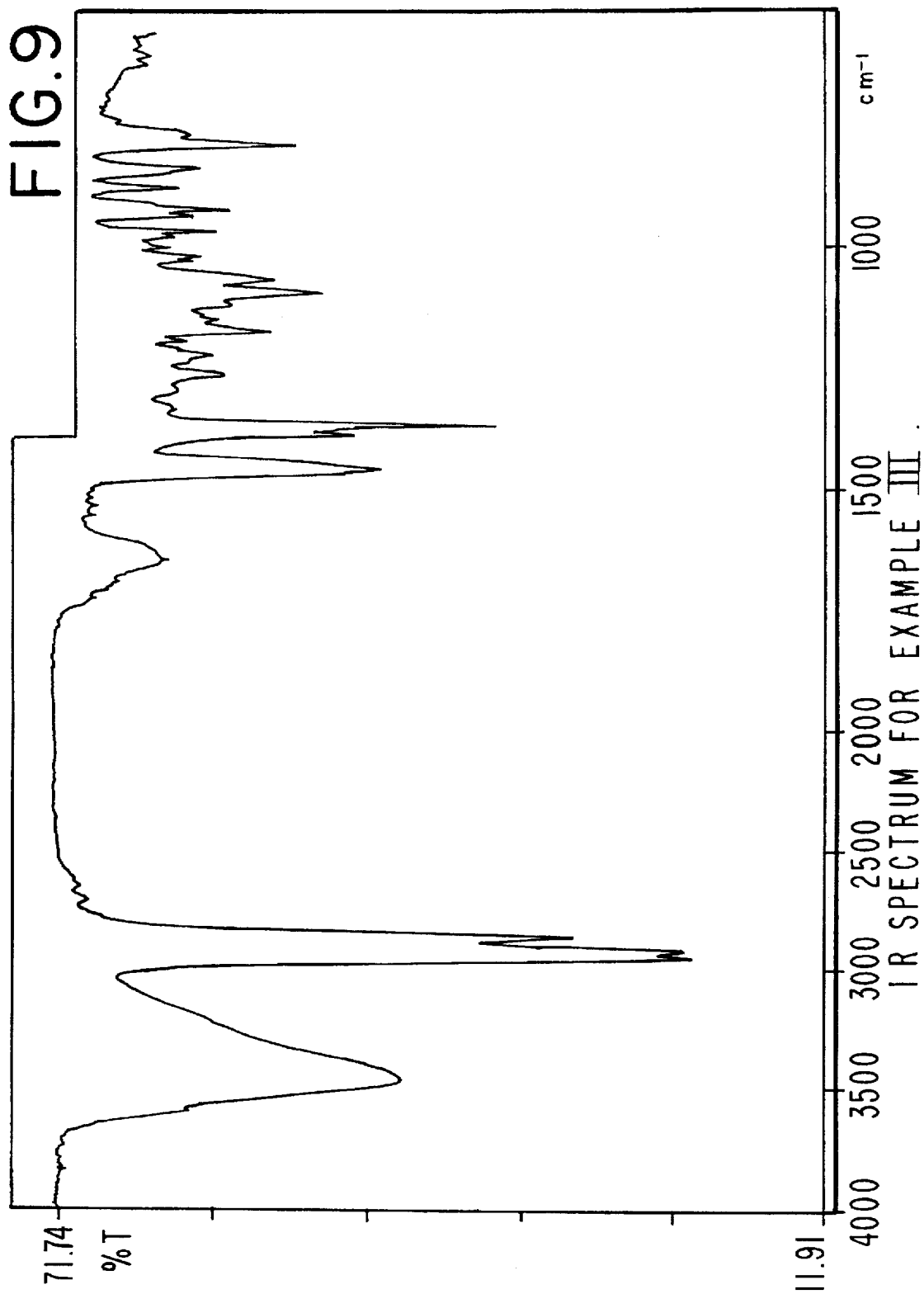

GLC PROFILE FOR EXAMPLE IV.

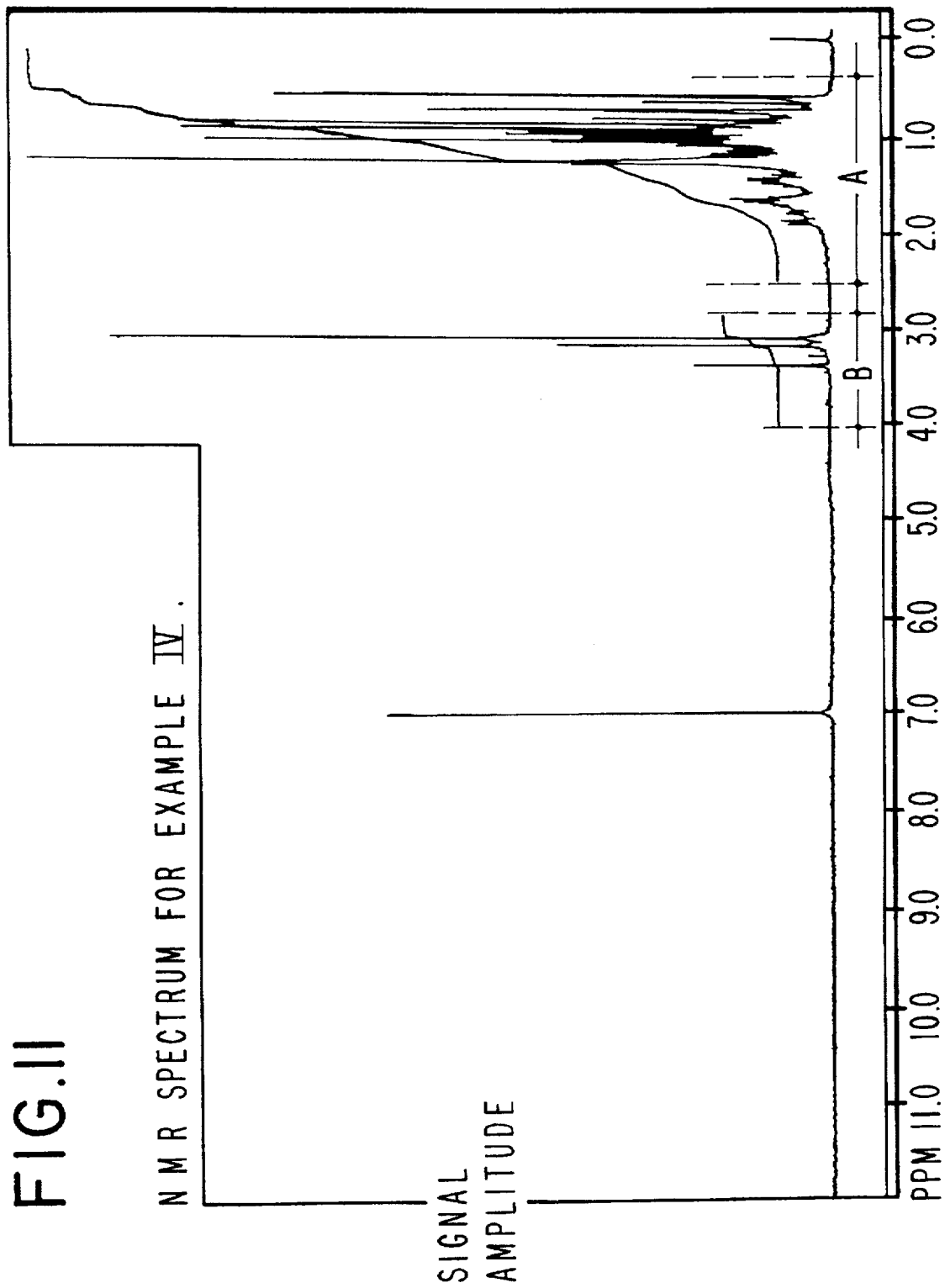

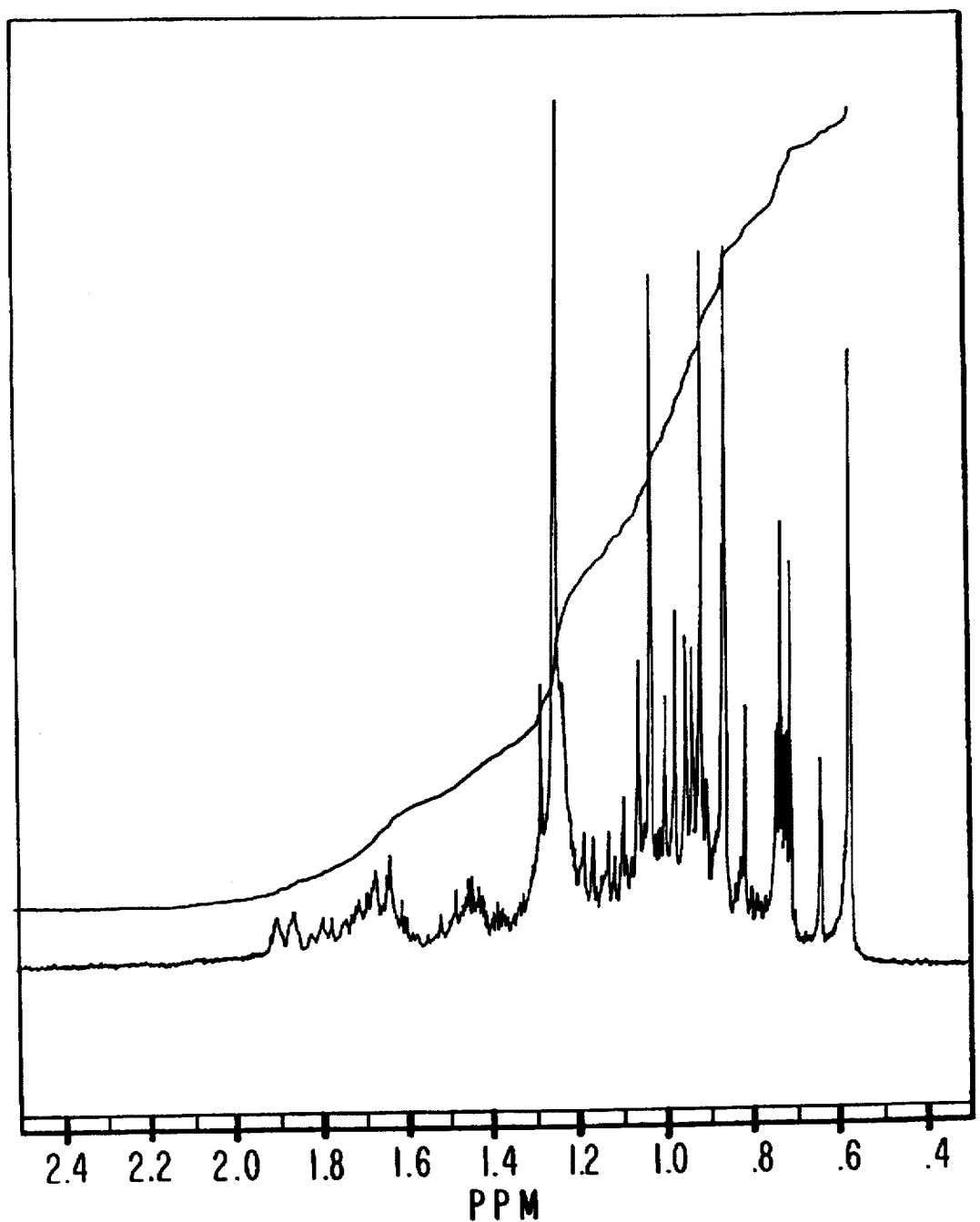
FIG.IIA

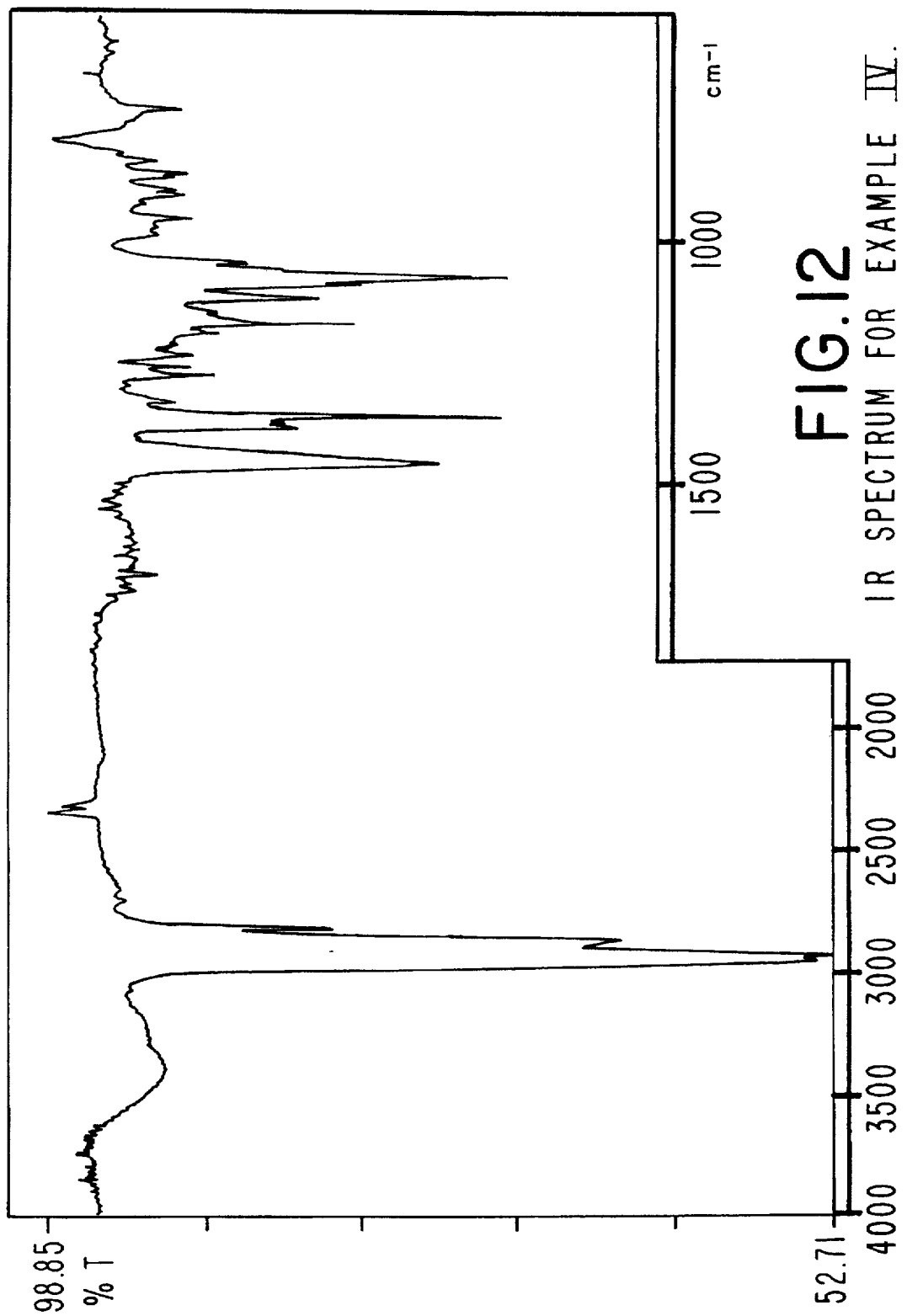
FIG. 12 IR SPECTRUM FOR EXAMPLE IV.

GLC PROFILE FOR EXAMPLE V.

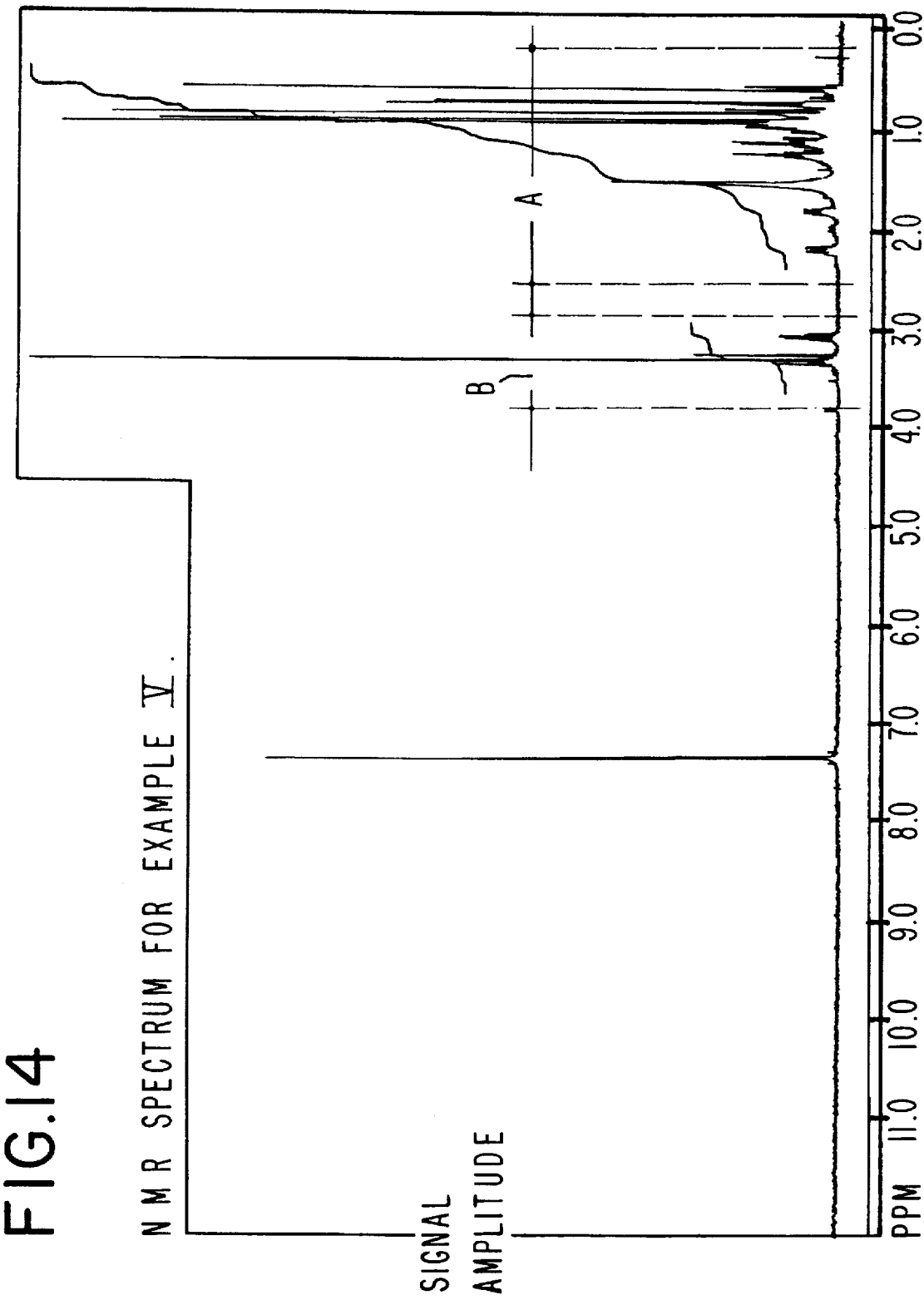
FIG. 14 NMR SPECTRUM FOR EXAMPLE V.

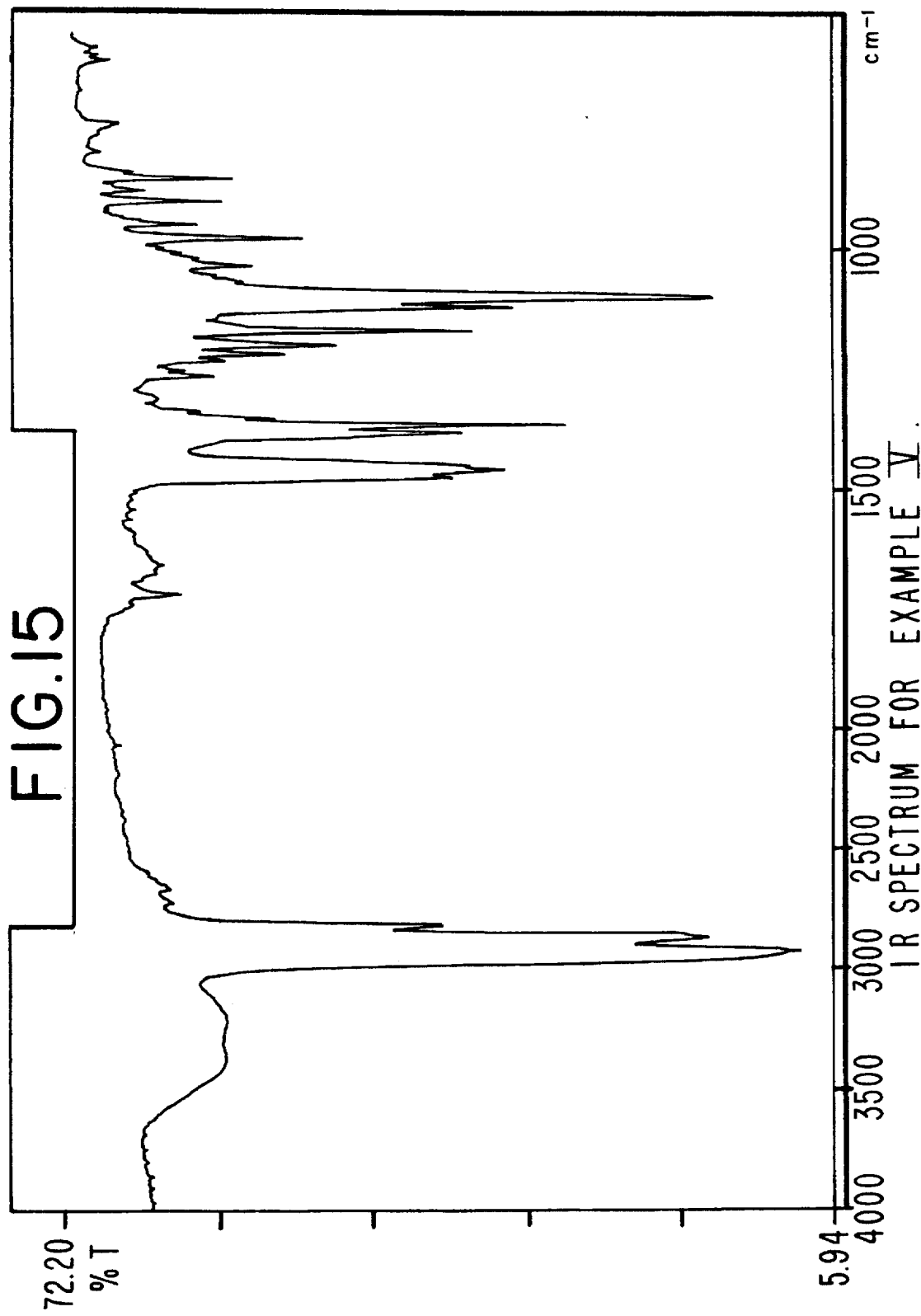
FIG.15 IR SPECTRUM FOR EXAMPLE V.

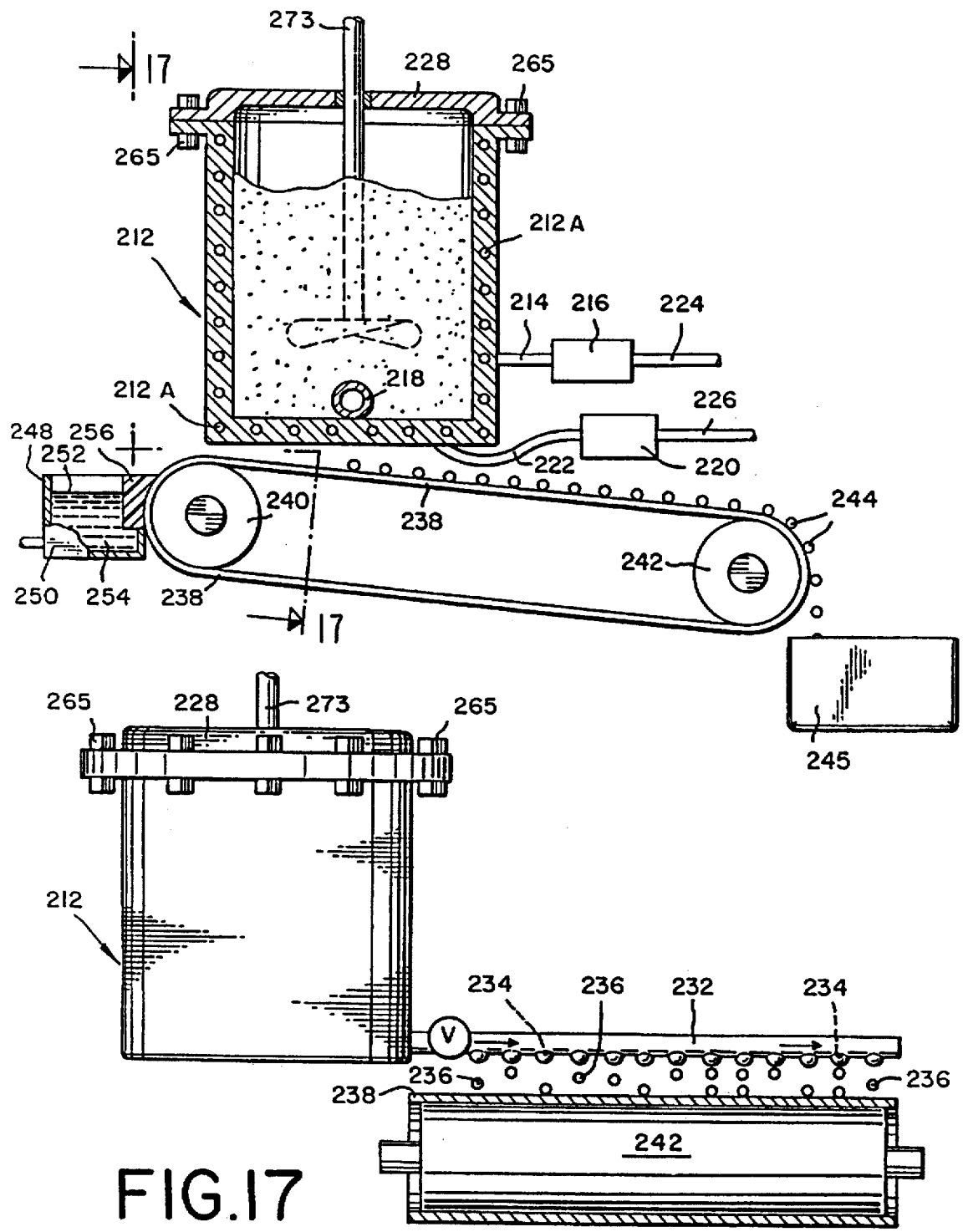

METHYL SUBSTITUTED HEXAHYDROINDANOLS AND ALKYL ETHERS THEREOF, ORGANOLEPTIC USES THEREOF, PROCESSES FOR PREPARING SAME AND PROCESS INTERMEDIATES THEREFOR

BACKGROUND OF THE INVENTION

The present invention relates to methyl substituted hexahydroindanols and alkyl ethers thereof defined according to the structure:

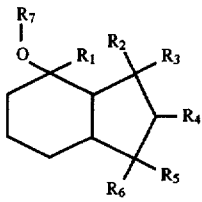

wherein $R_7$ represents hydrogen or $C_1$-$C_3$ alkyl; wherein $R_1$ represents methyl or ethyl; wherein $R_4$ represents methyl or hydrogen; and wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl and uses of such compositions in augmenting, enhancing or imparting an aroma in or to perfume compositions, perfumed articles and colognes. The present invention also relates the substantially pure composition of matter which is a mixture defined according to the structure:

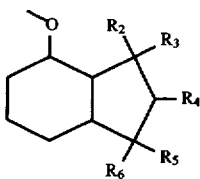

wherein in the mixture in each of the compounds, $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl and uses of these mixtures which are actually substantially pure mixtures of compounds having the structures:

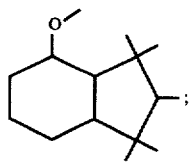

-continued

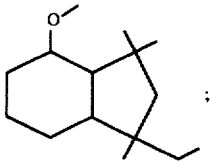
; and

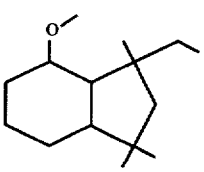

in augmenting or enhancing the aroma of perfume compositions, perfumed articles and colognes.

There has been considerable work performed relating to substances which can be used to impart (modify, augment or enhance) fragrances to (or in) various consumable materials. Such substances are used to diminish the use of expensive natural materials some of which may be in short supply and to provide more uniform properties in the finished products.

Woody, amber, cedarwood, fresh-cut cedarwood, fruity, bois ambrene, limlewood (fir), green, green wood, balsamic, cassis, juniper, animalic, musky, camphoraceous, jasmine and fatty aromas with woody, cedarwood, amber, fruity, sandalwood, musky, kephalis, green and balsamic topnotes are particularly desirable in several types of perfume compositions, perfumed articles and colognes.

Methyl substituted hexahydroindanols and alkyl ethers of methyl substituted hexahydroindanols are known to be useful in the field of perfumery.

Thus, Hall, et al. U.S. Pat. No. 4,535,192 having an effective date of Mar. 14, 1984 discloses the compound having the structure:

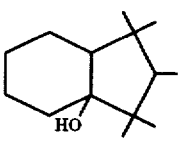

for use in perfumery. Hall, et al describes the organoleptic properties of the compound having the structure:

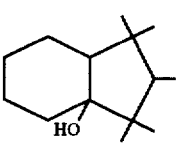

as "patchouli-like, piney, rooty, woody and camphoraceous with rooty, earthy, camphoraceous, woody and piney undertones".

Theimer, I, U.S. Pat. No. 3,767,713 having an effective date of Aug. 18, 1969 discloses the genus of compounds which are ethers having the generic structure:

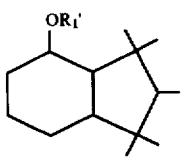

wherein $R_1'$ is $C_1$–$C_5$ alkyl. Theimer, I, discloses such compounds (as a broad genus) as having woody and amber odors.

Theimer, II, U.S. Pat. No. 3,681,464 having an effective date of Aug. 18, 1969 discloses the compound having the structure:

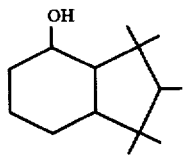

as having a woody and amber odor and discloses its use in perfumery.

Although the genus of compounds having the structure:

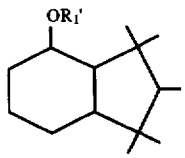

is disclosed as being useful in perfumery, the specific selected mixture defined according to the structure:

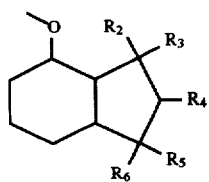

consisting of the compounds having the structures:

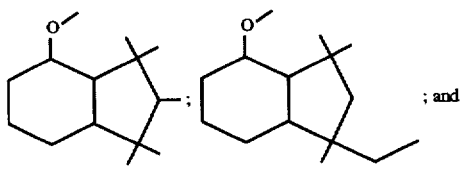

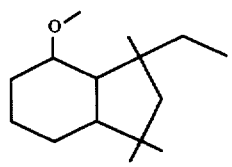

has unique, unexpected, advantageous organoleptic properties insofar as strength, substantivity and quality when compared to the other members of the genus having the structure:

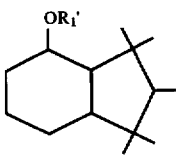

disclosed by U.S. Pat. No. 3,767,713. Furthermore, the genus defined according to the structure:

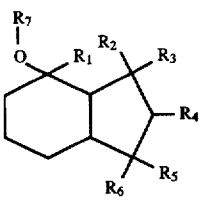

has, insofar as its individual components and mixtures thereof are concerned, unexpected, unobvious and advantageous organoleptic properties with respect to the prior art compounds having the structures:

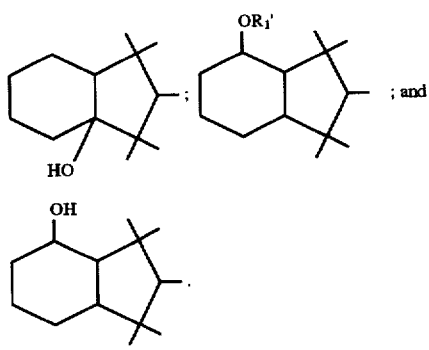

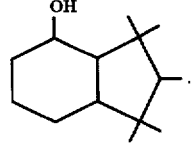

BRIEF DESCRIPTION OF THE DRAWINGS

FIG. 1 is the GLC profile for the reaction product of Example I containing the mixture of compounds defined according to the structure:

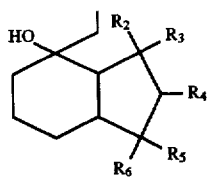

which is the mixture of the compounds having the structures:

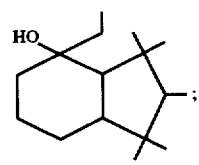

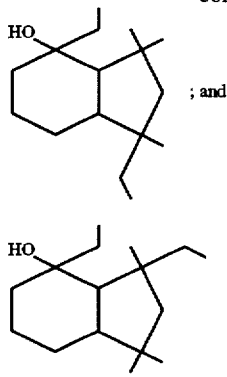

wherein $R_2$, $R_3$, $R_4$, $R_5$ and $R_6$ are defined, supra (conditions: SE-30 column programmed from 100°–220° C. at 8° C. per minute).

FIG. 2 is an NMR spectrum for the mixture of compounds defined according to the structure:

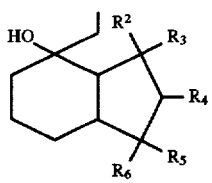

prepared according to Example I.

Figure 2A:
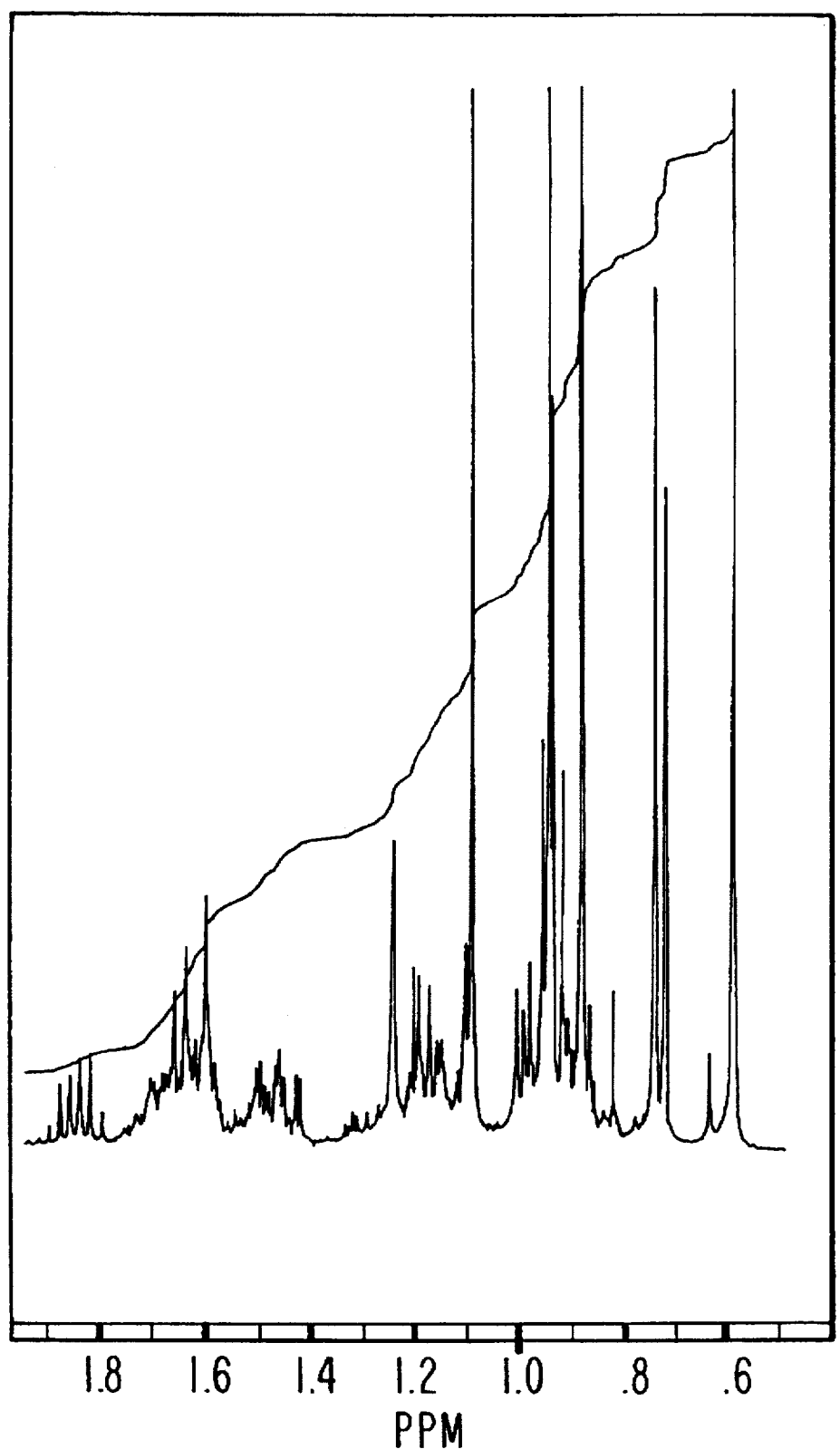

FIG. 2A is an enlargement of section "A" of the NMR spectrum of FIG. 2.

FIG. 3 is an infrared spectrum for the mixture of compounds defined according to the structure:

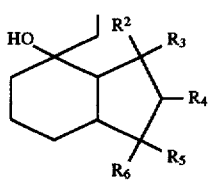

prepared according to Example I.

Figure 4:
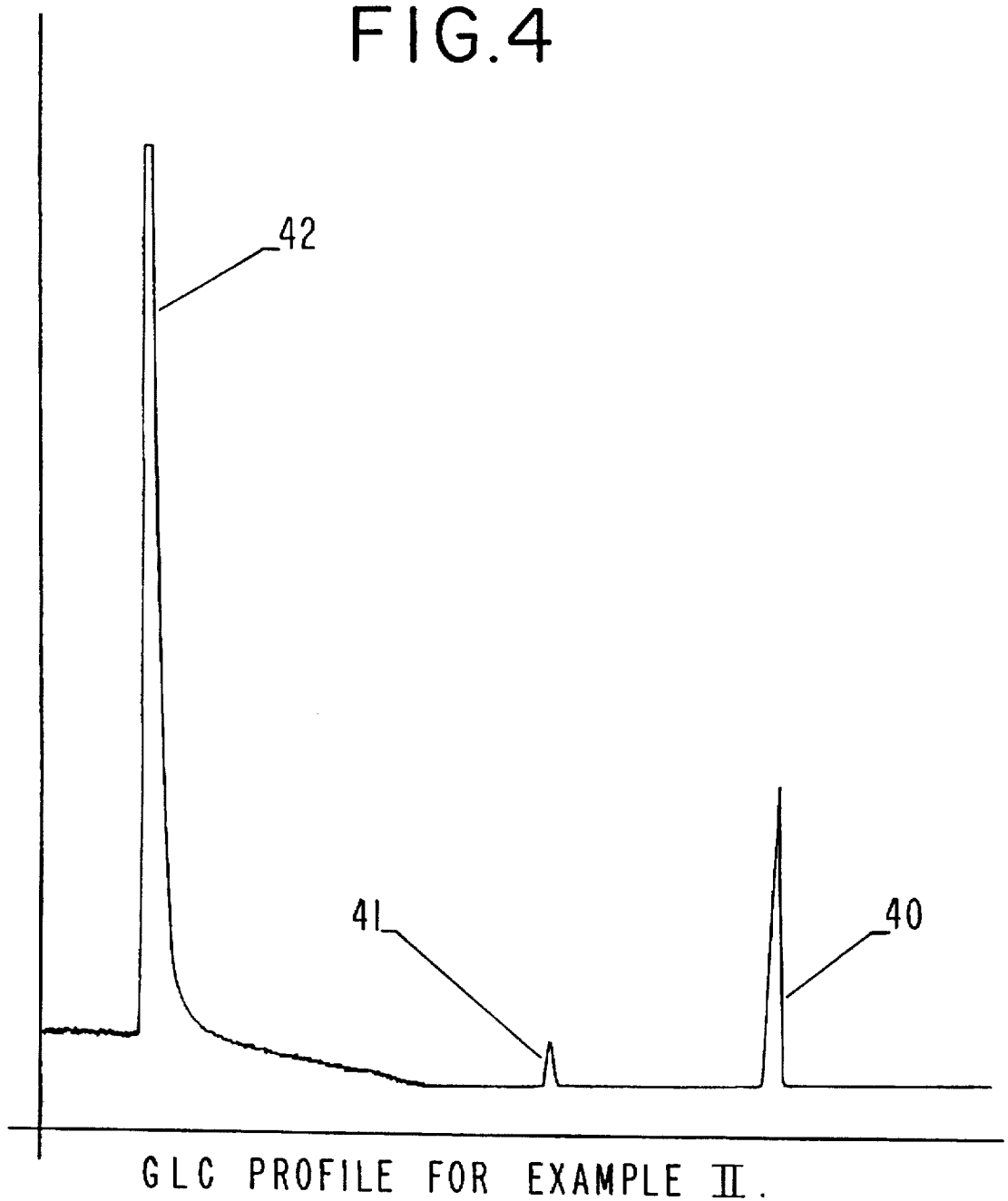

FIG. 4 is the GLC profile for the reaction product of Example II containing the mixture of compounds defined according to the structure:

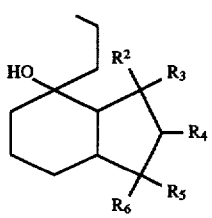

which is a mixture of compounds having the structures:

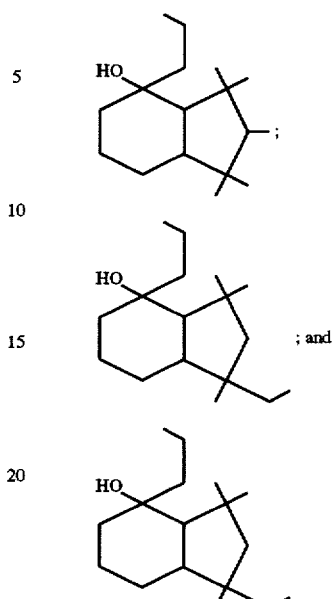

wherein $R_2$, $R_3$, $R_4$, $R_5$ and $R_6$ are defined, supra (conditions: SE-30 column programmed from 150°–220° C. at 8° C. per minute).

FIG. 5 is the NMR spectrum for the mixture of compounds defined according to the structure:

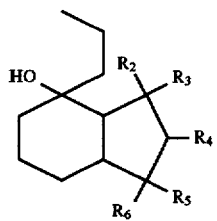

prepared according to Example II.

Figure 5A:
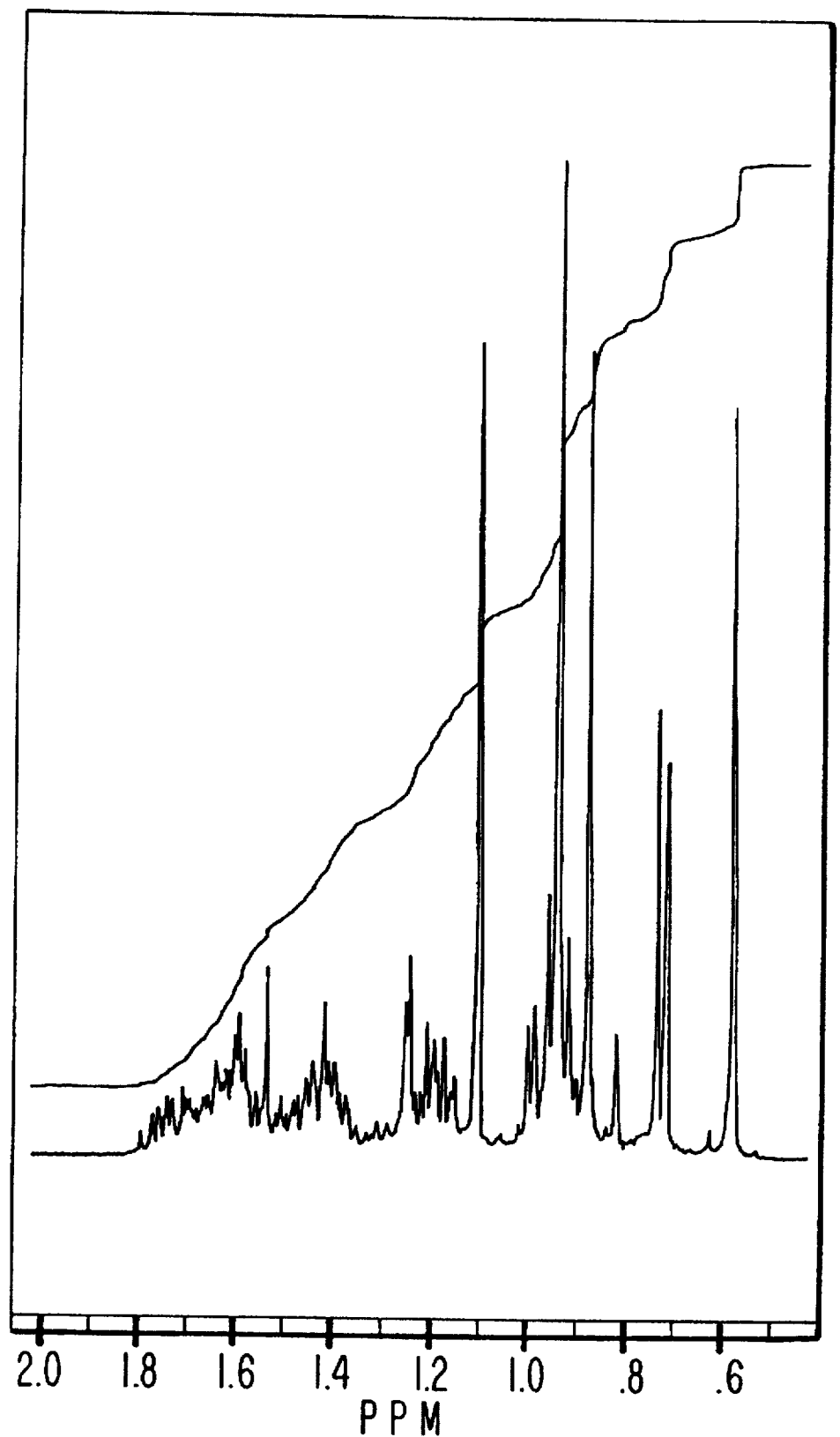

FIG. 5A is an enlargement of section "A" of the NMR spectrum of FIG. 5.

FIG. 6 is the infrared spectrum for the mixture of compounds defined according to the structures:

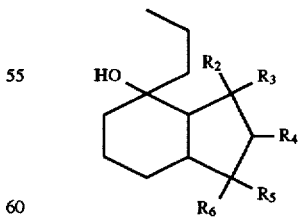

prepared according to Example II.

Figure 7:
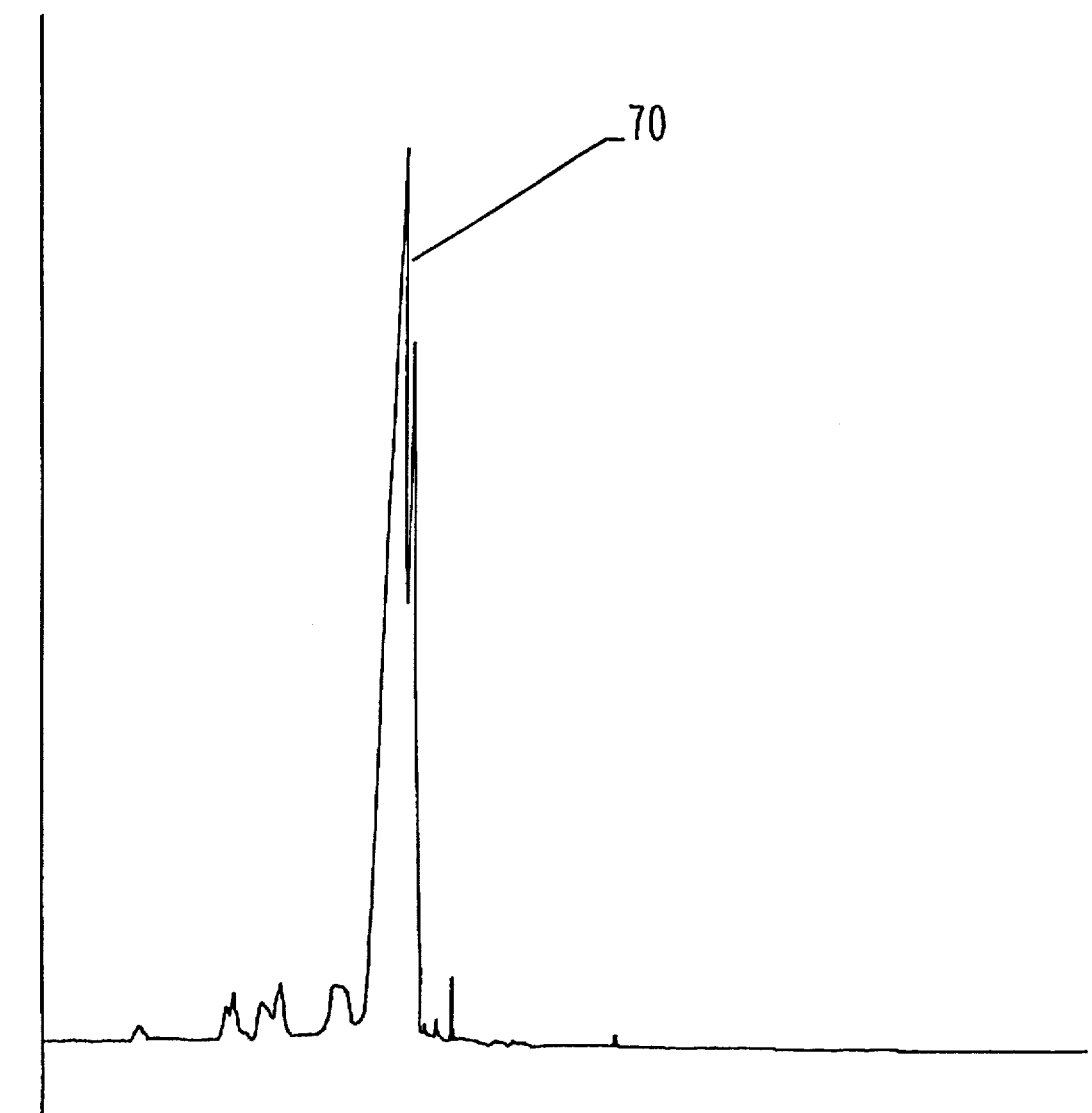

FIG. 7 is the GLC profile for the reaction product of Example III containing the mixture of compounds defined according to the structure:

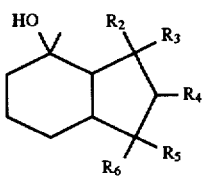

which includes the compounds having the structures:

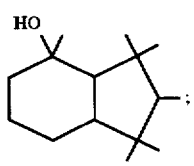

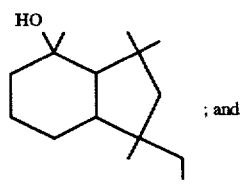
; and

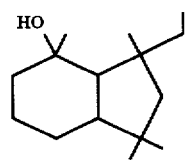

(conditions: SE-30 column programmed from 150°–220° C. at 8° C. per minute).

FIG. 8 is the NMR spectrum for the mixture of compounds defined according to the structure:

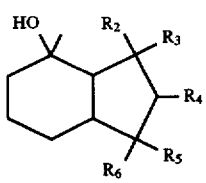

prepared according to Example III.

Figure 8A:
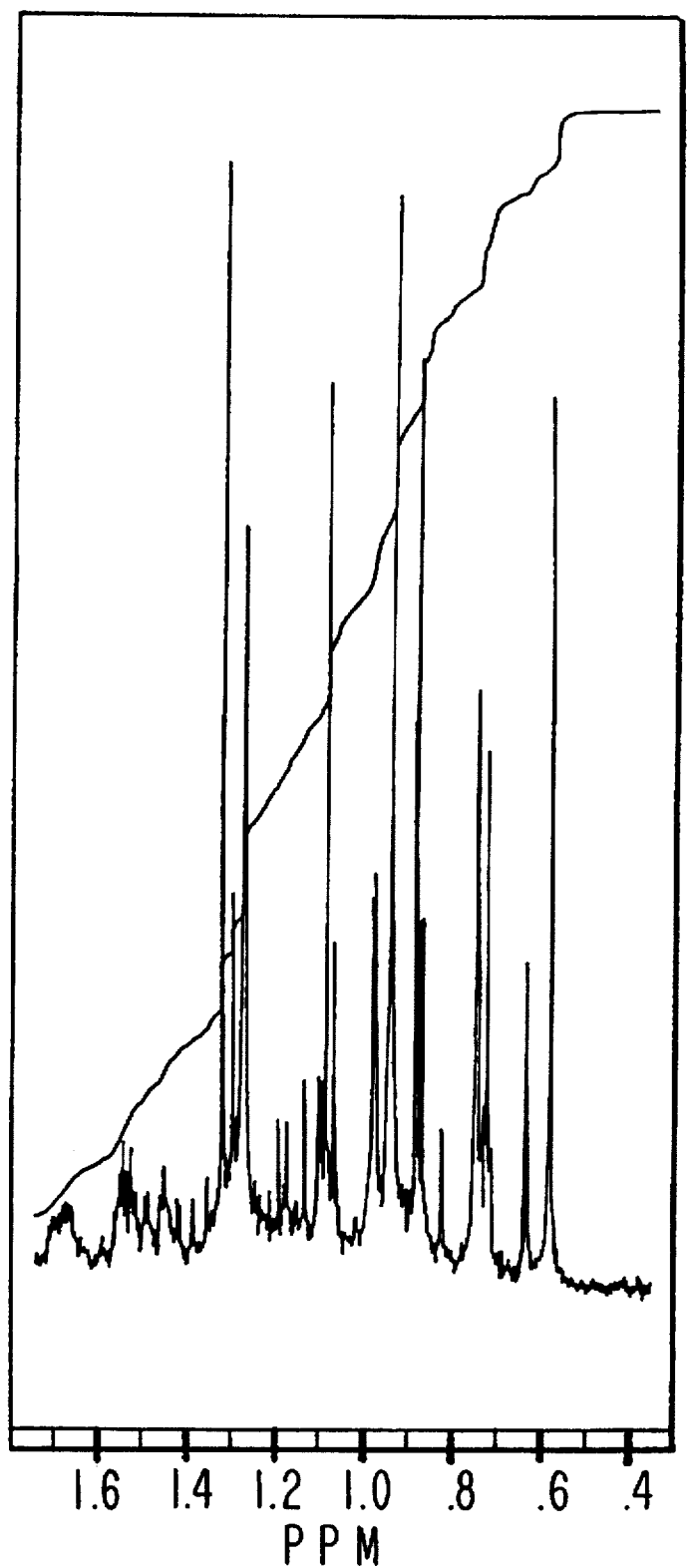

FIG. 8A is an enlargement of section "A" of the NMR spectrum of FIG. 8.

FIG. 9 is the infrared spectrum for the mixture of compounds defined according to the structure:

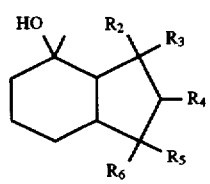

prepared according to Example III (wherein $R_2$, $R_3$, $R_4$, $R_5$ and $R_6$ are defined, supra).

Figure 10:
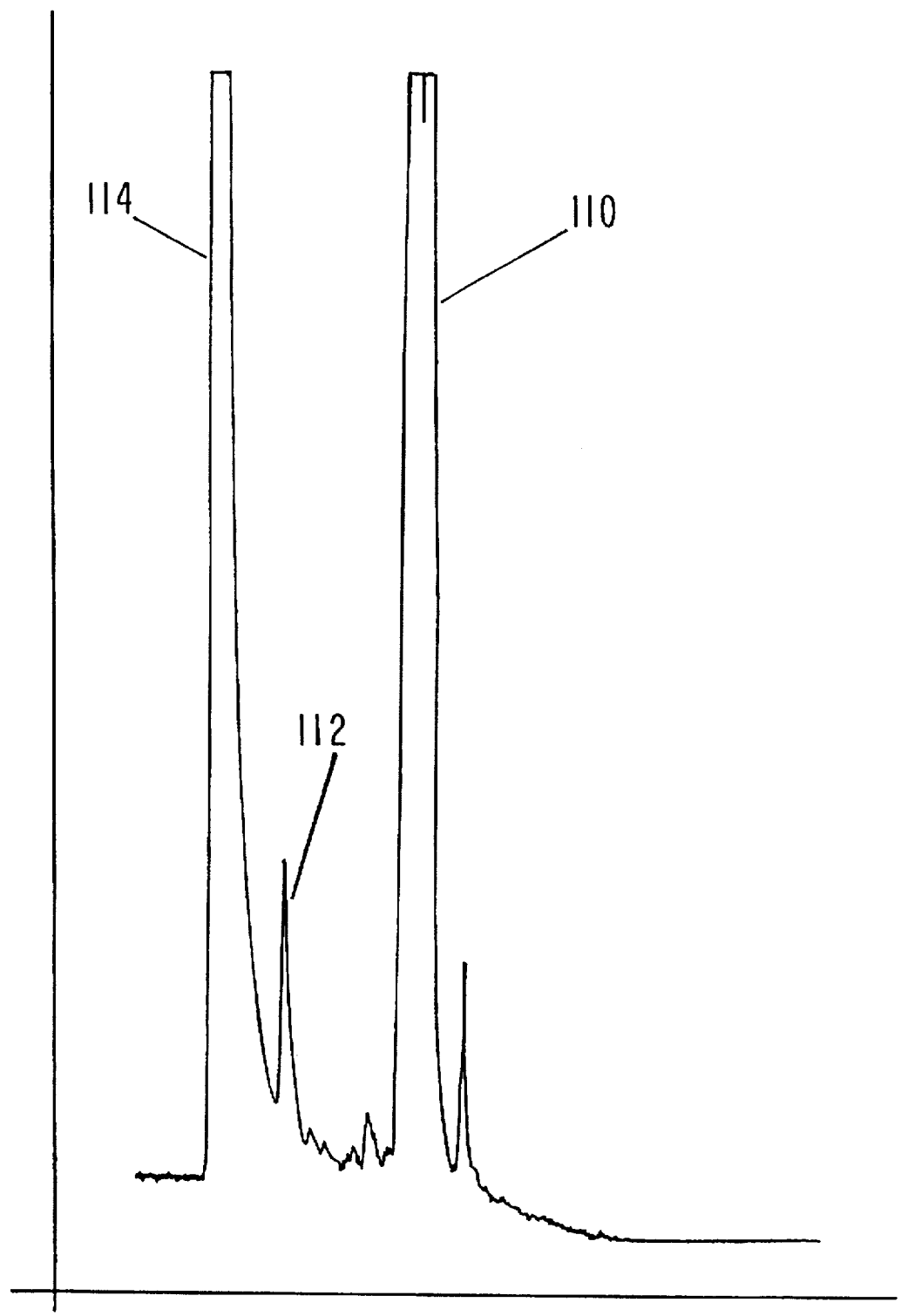

FIG. 10 is the GLC profile for the reaction product of Example IV containing the mixture of compounds defined according to the structure:

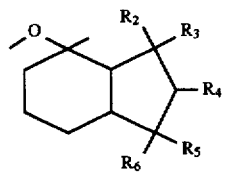

which is a mixture of compounds having the structures:

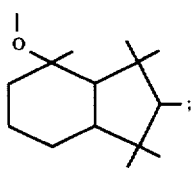

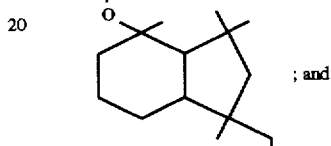
; and

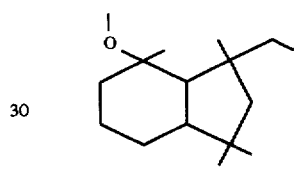

wherein $R_2$, $R_3$, $R_4$, $R_5$ and $R_6$ are defined, supra (conditions: SE-30 column programmed from 150°–220° C. at 8° C. per minute).

FIG. 11 is the NMR spectrum for the mixture of compounds defined according to the structure:

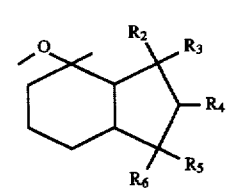

prepared according to Example IV.

FIG. 11A is an enlargement of section "A" of the NMR spectrum of FIG. 11.

Figure 11B:
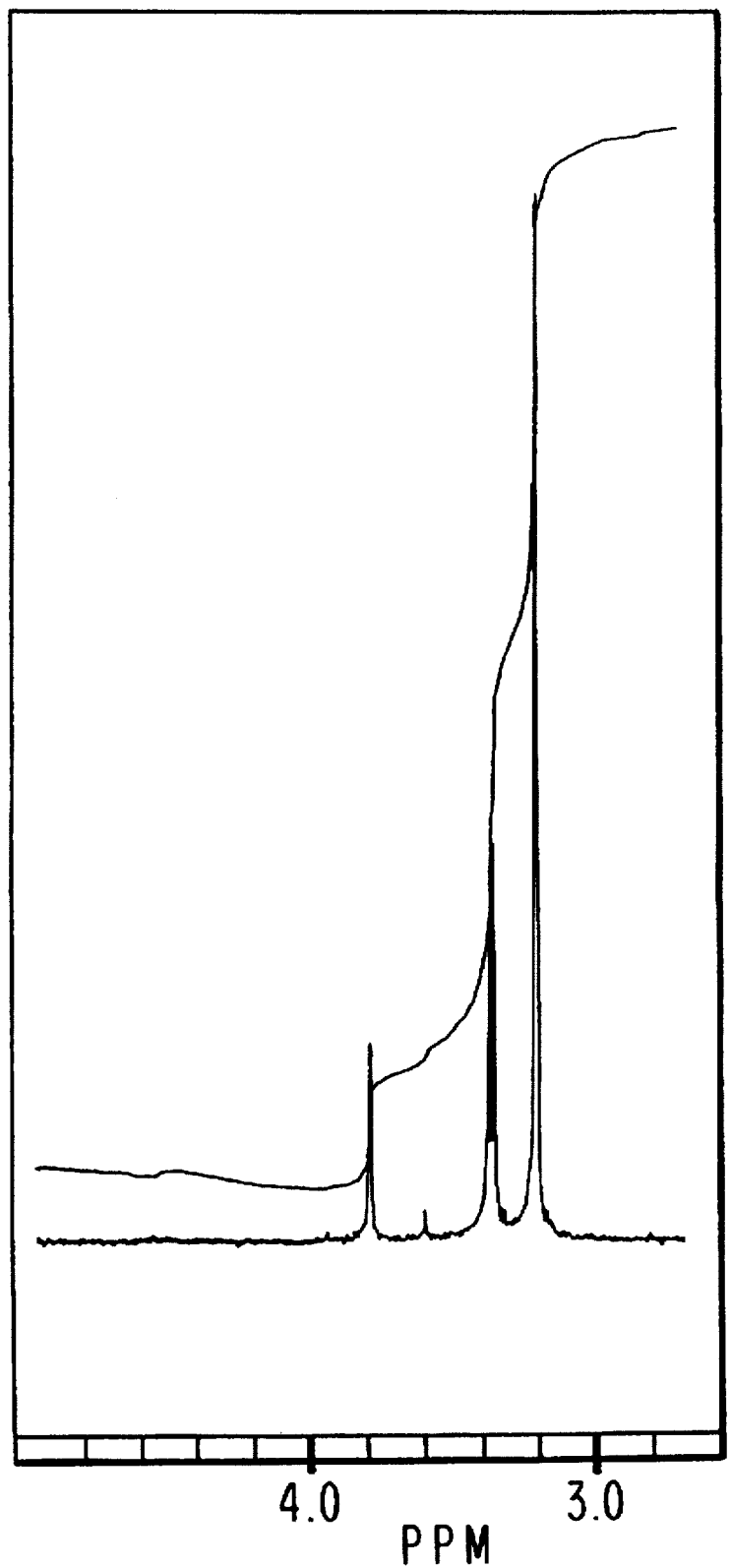

FIG 11B is an enlargement of section "B" of the NMR spectrum of FIG. 11.

FIG. 12 is the infrared spectrum for the mixture of compounds defined according to the structure:

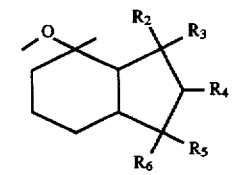

prepared according to Example IV.

Figure 13:
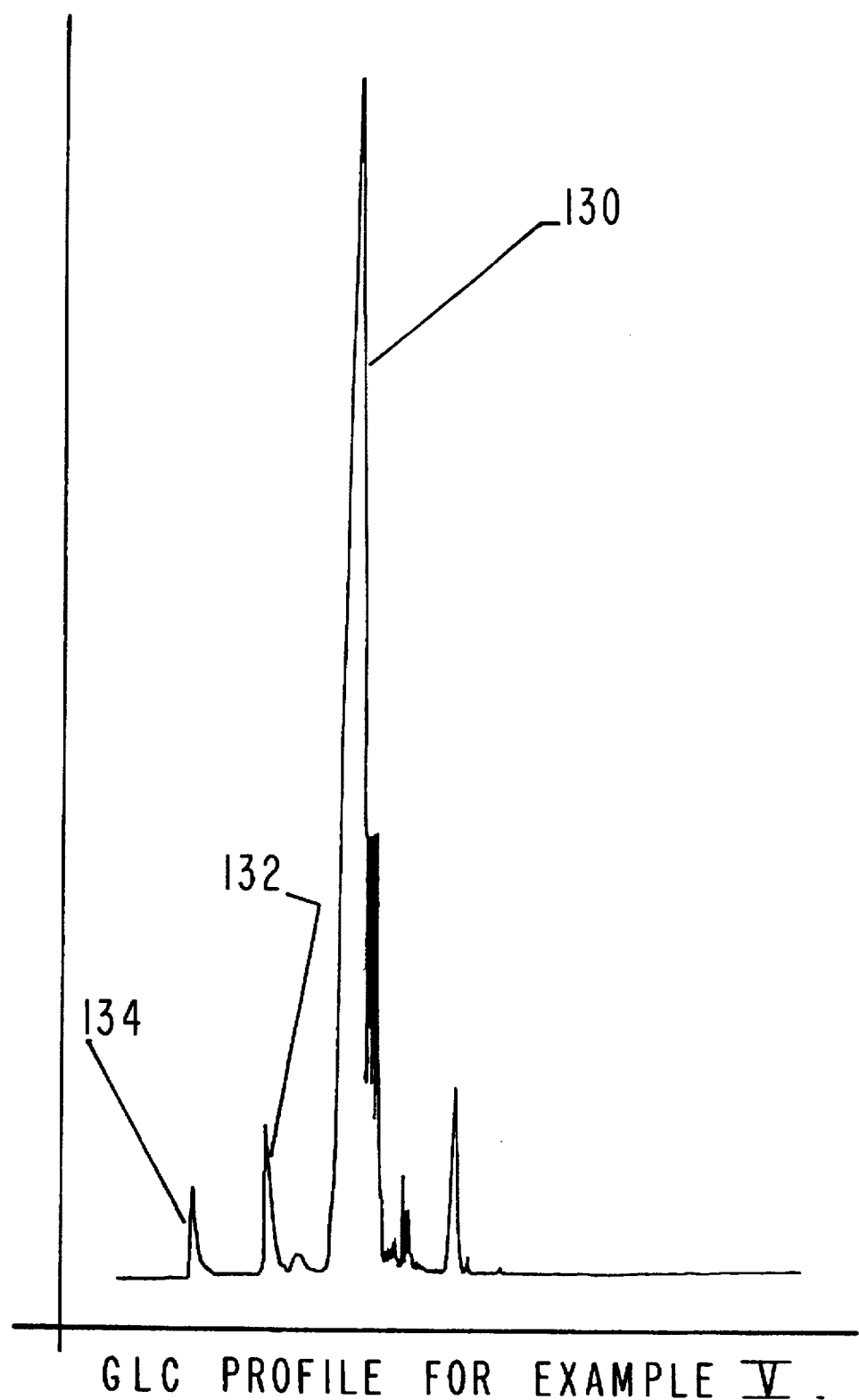

FIG. 13 is the GLC profile for the reaction product of Example V containing the mixture of compounds defined according to the structure:

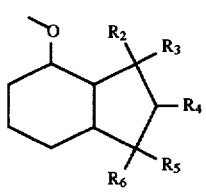

which is a mixture of the compounds having the structures:

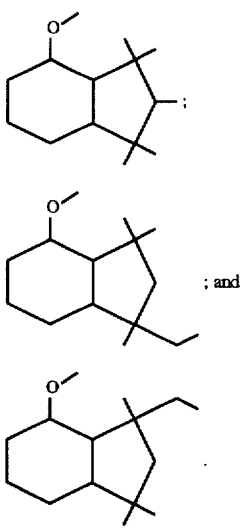

wherein $R_2$, $R_3$, $R_4$, $R_5$ and $R_6$ are defined, supra (conditions: SE-30 column programmed at 150°–220° C. from 8° C. per minute).

FIG. 14 is the NMR spectrum for the mixture of compounds having the structure:

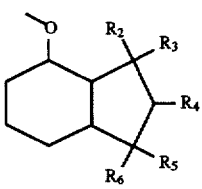

prepared according to Example V.

Figure 14A:
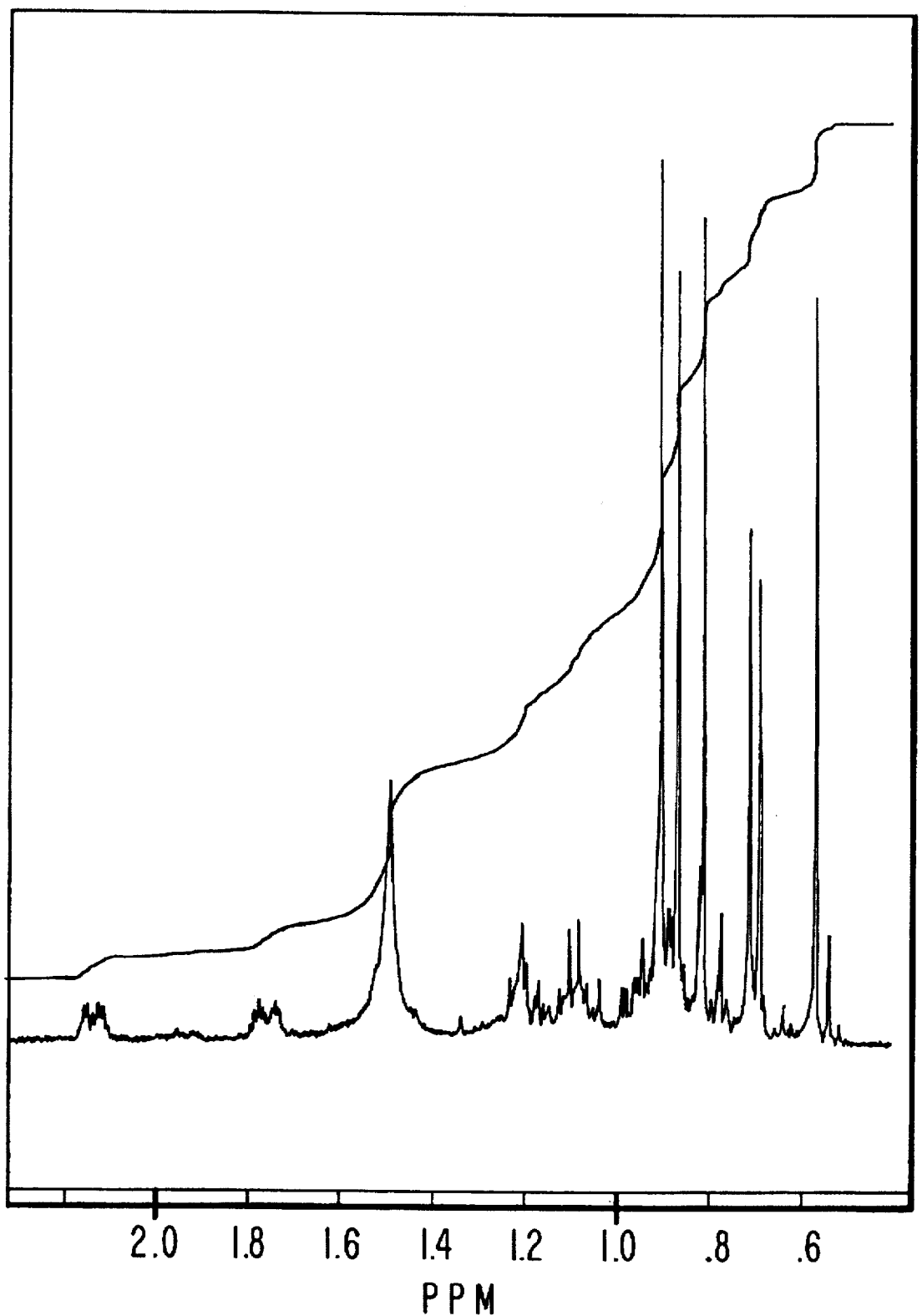

FIG. 14A is an enlargement of section "A" of the NMR spectrum of FIG. 14.

Figure 14B:
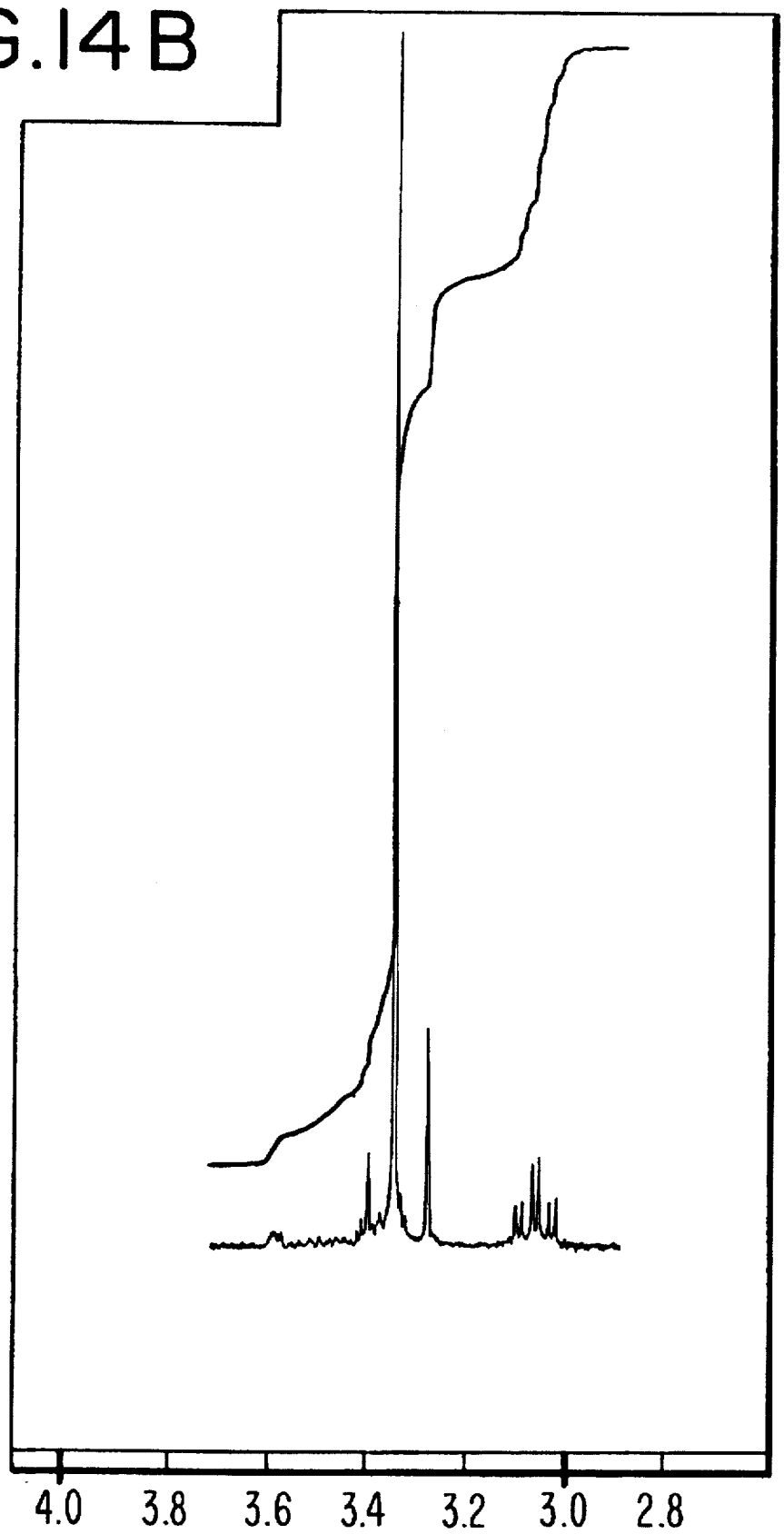

FIG. 14B is an enlargement of section "B" of the NMR spectrum of FIG. 14.

FIG. 15 is the infrared spectrum for the mixture of compounds having the structure:

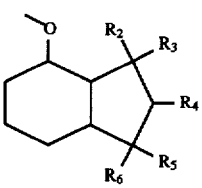

prepared according to Example V.

FIG. 16 represents a cutaway side elevation view of apparatus used in forming perfumed polymers which contain embedded therein at least one of the methyl substituted hexahydroindanols and alkyl ethers thereof of our invention.

FIG. 17 is a front view of the apparatus of FIG. 16 looking in the direction of the arrows along lines 17–17.

DETAILED DESCRIPTION OF THE DRAWINGS

FIG. 1 is the GLC profile for the reaction product of Example I. The peak indicated by reference numeral 10 is the peak for the mixture of compounds defined according to the structure:

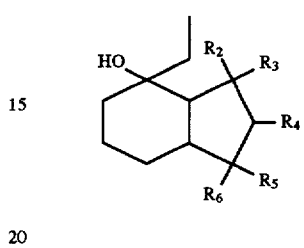

which is a mixture of the compounds having the structures:

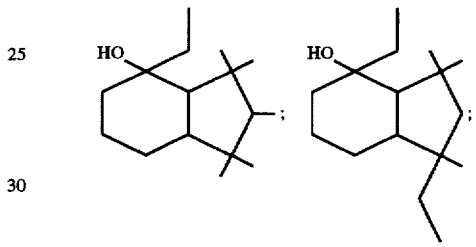

and

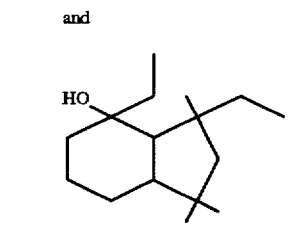

wherein $R_2$, $R_3$, $R_4$, $R_5$ and $R_6$ are defined, supra.

The peak indicated by reference numeral 11 is the peak for the mixture of reactants defined according to the structure:

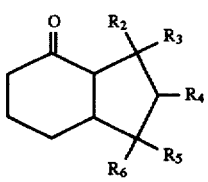

which is a mixture of the compounds having the structures:

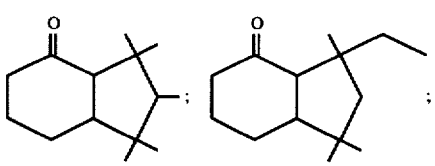

and

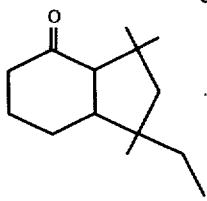

The peak indicated by reference numeral 12 is the peak for the mixture of hydrocarbons defined according to the structure:

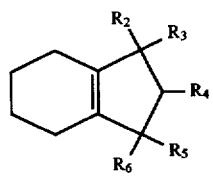

which is a mixture of the compounds having the structures:

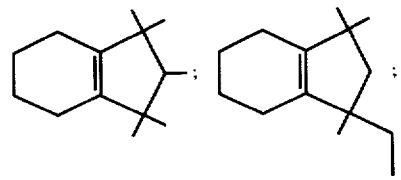

and

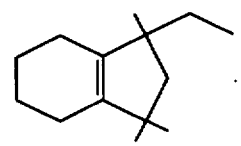

The peak indicated by reference numeral 14 is the peak for the reaction solvent, tetrahydrofuran.

FIG. 4 is the GLC profile for the reaction product of Example II. The peak indicated by reference numeral 40 is the peak for the mixture of compounds having the structure:

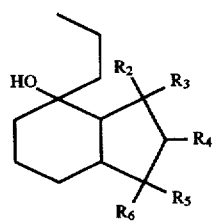

which is a mixture of the compounds having the structures:

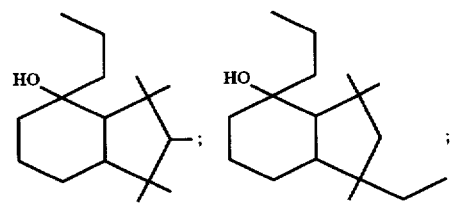

and

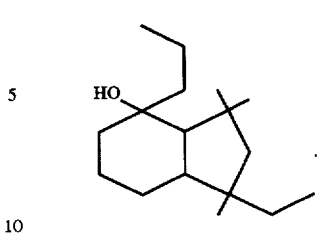

The peak indicated by reference numeral 41 is the peak for the starting material defined according to the structure:

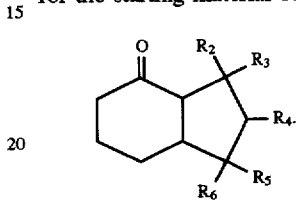

The peak indicated by reference numeral 42 is the peak for the reaction solvent, tetrahydrofuran.

FIG. 7 is the GLC profile for the reaction product of Example III. The peak indicated by reference numeral 70 is the peak for the mixture of compounds having the structure:

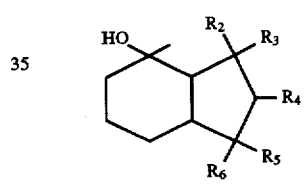

which is a mixture of the compounds having the structures:

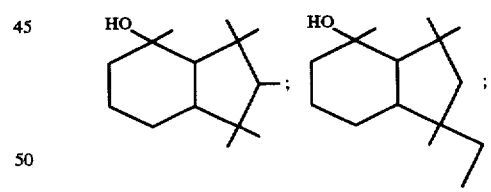

and

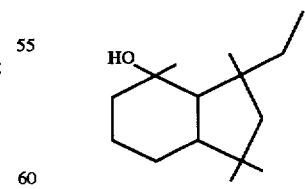

FIG. 10 is the GLC profile for the reaction product of Example IV. The peak indicated by reference numeral 110 is the peak for the mixture of compounds defined according to the structure:

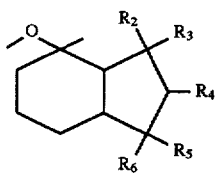

which is a mixture of the compounds having the structures:

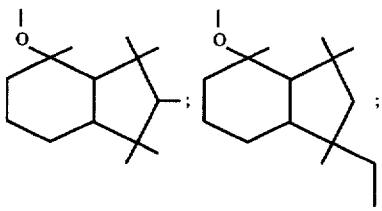

and

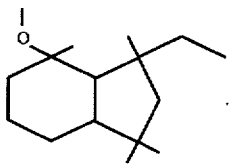

The peak indicated by reference numeral 112 is the peak for the hydrocarbons defined according to the structure:

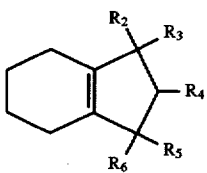

which is a mixture of the compounds having the structures:

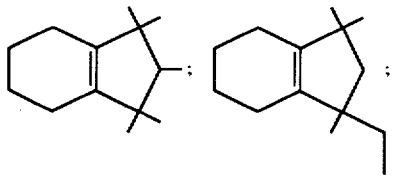

and

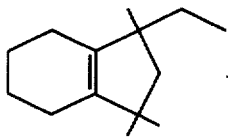

The peak indicated by reference numeral 114 is for the reaction solvent, tetrahydrofuran.

FIG. 13 is the GLC profile for the reaction product of Example V. The peak indicated by reference numeral 130 is the peak for the mixture of compounds defined according to the structure:

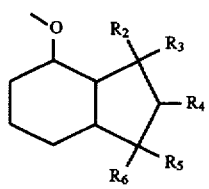

which is a mixture of the compounds having the structures:

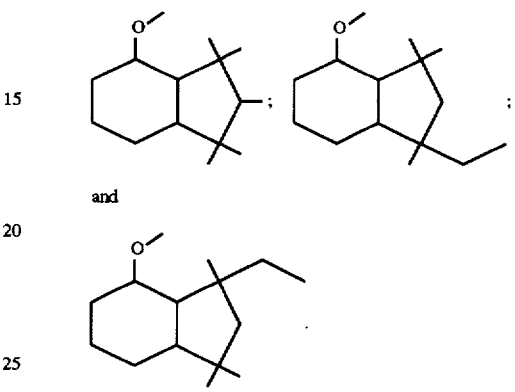

The peak indicated by reference numeral 132 is the peak for the hydrocarbon mixture defined according to the structure:

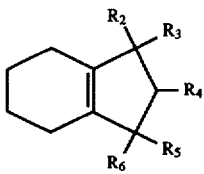

which is a mixture of the compounds having the structures:

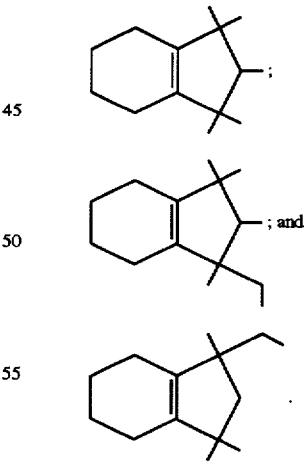

The peak indicated by reference numeral 134 is the peak for the reaction solvent, tetrahydrofuran.

Referring to FIGS. 16 and 17, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit (indicated by reference numeral 218). Thus, referring to FIGS. 16 and 17, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the methyl substituted hexahydroindanols and alkyl ethers thereof of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Sayboldt seconds. The heater is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the methyl substituted hexahydroindanols and alkyl ethers thereof of our invention is quickly added to the melt. Generally, about 10–45% by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also shown by reference numeral 218 (in cutaway cross section)) having a multiplicity of orifices 234 adjacent to the lower side thereof. The outer end of the conduit 232 is closed so that the liquid polymer in intimate admixture with one or more of the methyl substituted hexahydroindanols and alkyl ethers thereof of our invention and one or more other substances (if desired) will continuously drop through the orifices 234 downwardly from the conduit 232. During this time, the temperature of the polymer intimately admixed with the perfumery substance in the container 212 is accurately controlled so that a temperature in the range of from about 240°–250° C., for example (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the methyl substituted hexahydroindanols and alkyl ethers thereof of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water 252 or some other suitable cooling liquid to insure the rapid cooling of each of the pellets 244. The pellets 244 are then collected from the container 245 and utilized for the formation of other functional products, e.g., garbage bags and the like.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

The present invention provides methyl substituted hexahydroindanols and alkyl ethers thereof defined according to the structure:

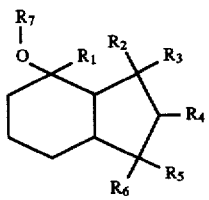

$R_7$ represents hydrogen or $C_1$–$C_3$ lower alkyl; wherein $R_1$ represents methyl or ethyl; wherein $R_4$ represents methyl or hydrogen; and wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl.

The present invention also provides substantially pure mixtures defined according to the structure:

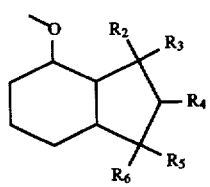

which are mixtures of the compounds having the structures:

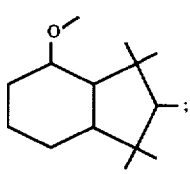

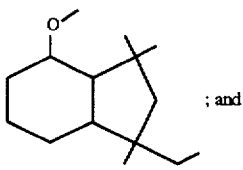
; and

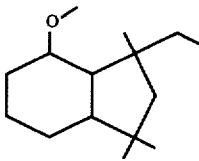

The methyl substituted hexahydroindanols and alkyl ethers thereof of our invention produced according to the processes of our invention are capable of augmenting, enhancing or imparting woody, amber, cedarwood, fresh cut cedarwood, fruity, bois ambrene, limlewood (fir), green, green wood, balsamic, cassis, juniper, animalic, musky, camphoraceous, jasmine and fatty aromas with woody, cedarwood, amber, fruity, sandalwood, musky, kephalis, green and balsamic topnotes in or to perfume compositions, colognes and perfumed articles (including soaps, anionic, cationic, nonionic or zwitterionic detergents, fabric softener articles, hair preparations and perfumed polymers).

The methyl substituted hexahydroindanols and alkyl ethers thereof of our invention are produced using as a starting material the mixture of ketones defined according to the structure:

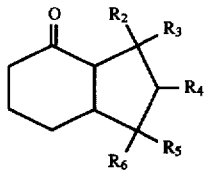

containing the compounds having the structures:

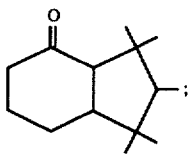

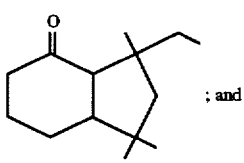
; and

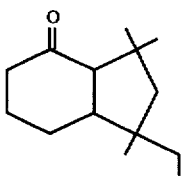

The mixture defined according to the structure:

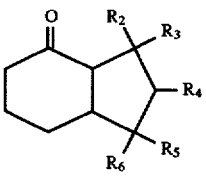

wherein $R_2$, $R_3$, $R_4$, $R_5$ and $R_6$ are defined, supra, is prepared according to the procedure set forth in Examples I and II at columns 5 and 6 of U.S. Pat. No. 3,681,464 issued on Aug. 1, 1972 (title: "SATURATED INDANE DERIVATIVES AND PROCESSES FOR PRODUCING SAME") wherein the reaction sequence:

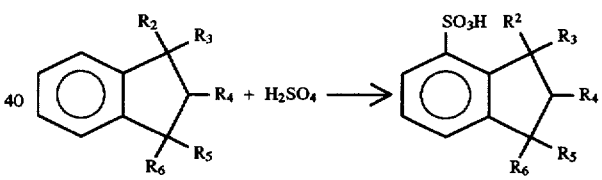

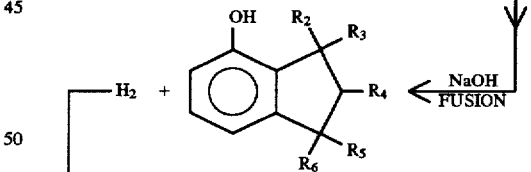

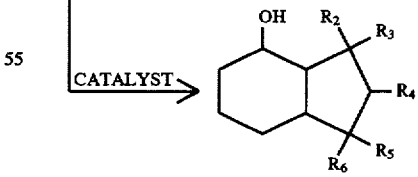

and

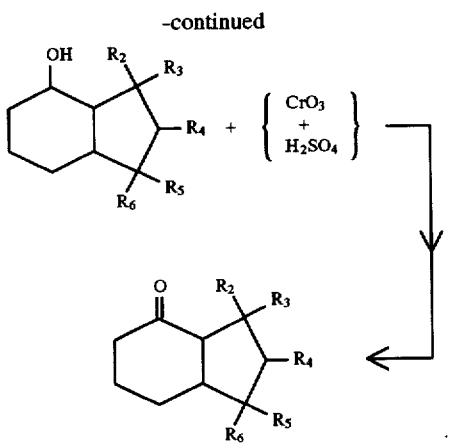

The mixture of compounds defined according to the structure:

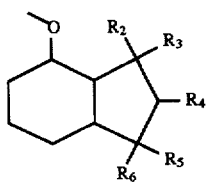

uses as a starting material the mixture of compounds defined according to the structure:

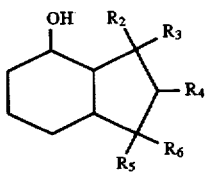

prepared according to the reaction sequence:

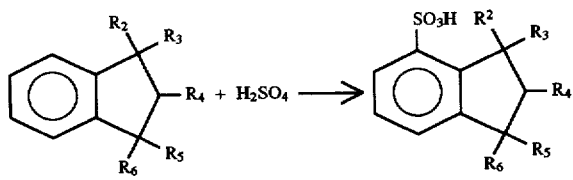

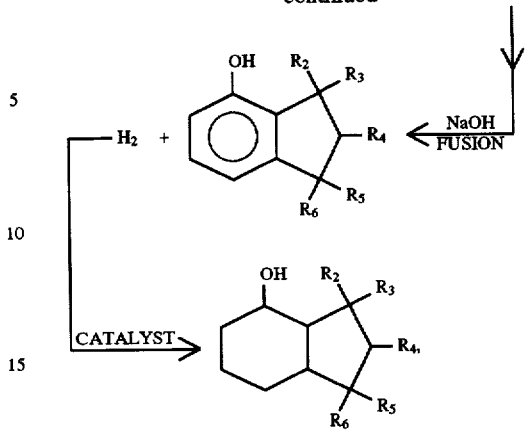

the details for which are disclosed in the above-mentioned U.S. Pat. No. 3,681,464 issued on Aug. 1, 1972, the specification for which is incorporated by reference herein.

With reference to preparing the methyl substituted hexahydroindanols and alkyl ethers thereof of our invention defined according to the structure:

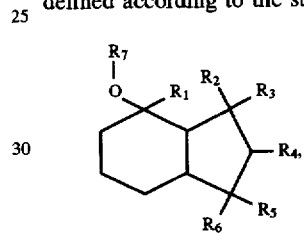

the mixture of ketones defined according to the structure:

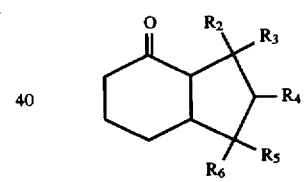

is reacted with an organometallic compound having the structure:

wherein $R_1$ is methyl or ethyl; wherein P is the valence of M''' which is 1 or 2; wherein M''' is a methyl or metal halide, M or M'; wherein M represents Li or MgX; wherein X is chloro, bromo or iodo; wherein M' is a bivalent metal, cadmium or zinc. Thus the compound having the structure:

may either be a compound having the structure:

in the case of monovalent metals or metal halides, or the compound having the structure:

in the case of bivalent metals. The reaction takes place at low temperatures, e.g., −10° C. up to +10° C. in the presence of a solvent which is inert to the reactants, that is, diethyl ether (anhydrous) or tetrahydrofuran (anhydrous).

This reaction is set forth as follows:

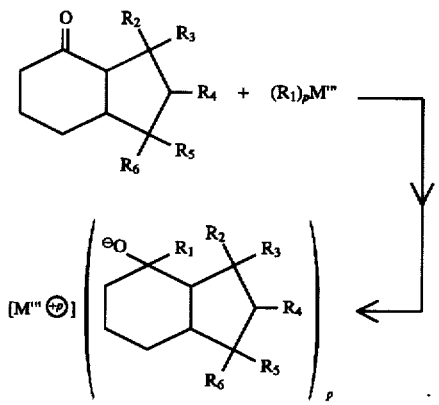

The resulting organometallic salt having the structure:

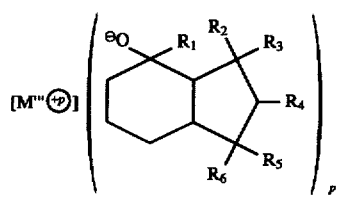

is then hydrolyzed in the presence of an acid, such as dilute hydrochloric acid or dilute ammonium chloride according to the reaction:

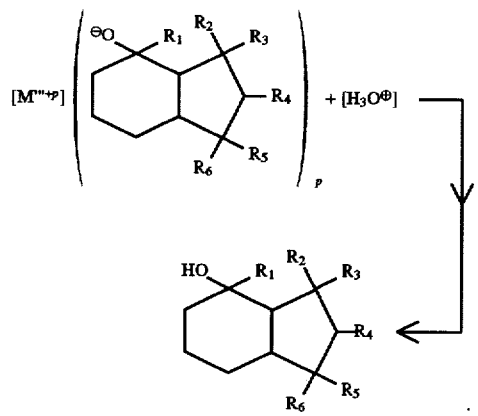

The resulting alcohol defined according to the structure:

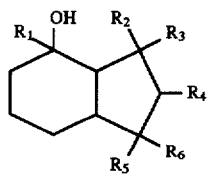

is then etherified with an alkyl halide defined according to the structure:

wherein $R_7$ is $C_1$–$C_3$ alkyl, that is, methyl, ethyl, n-propyl or isopropyl and Y represents chloro, bromo or iodo according to the reaction sequence:

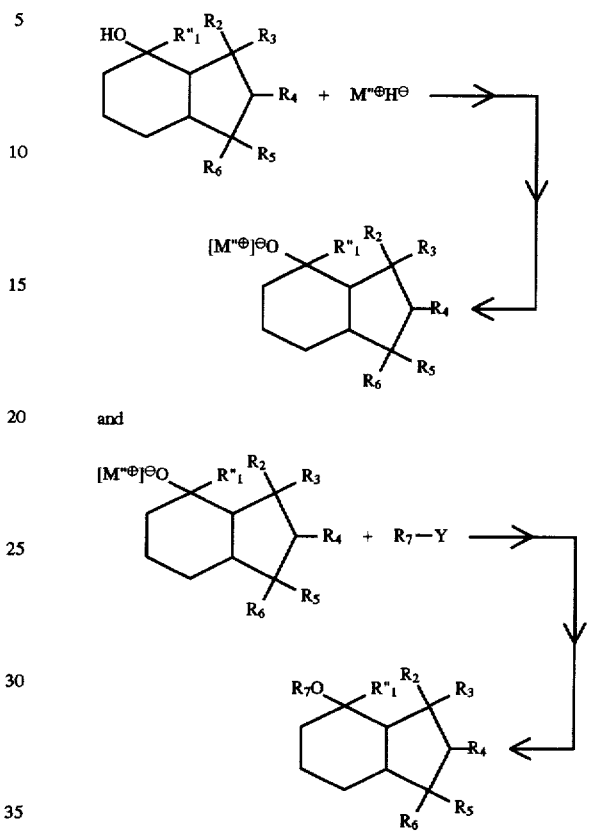

wherein $R_1''$ represents hydrogen, methyl or ethyl. It is to be noted then that the mixtures defined according to the structure:

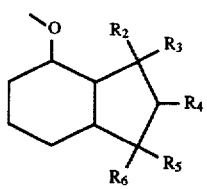

and the methyl substituted hexahydroindanols and alkyl ethers thereof defined according to the structure:

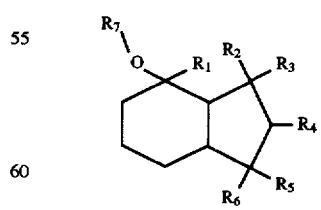

can both be prepared in this manner.

In carrying out the etherification reaction, the mixture of compounds defined according to the structure:

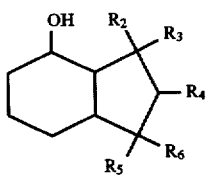

or the compounds defined according to the structure:

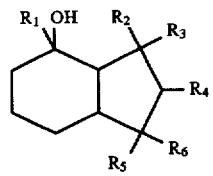

are first reacted with an alkali metal hydride having the formula:

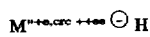

wherein M'' is sodium or potassium according to the reaction:

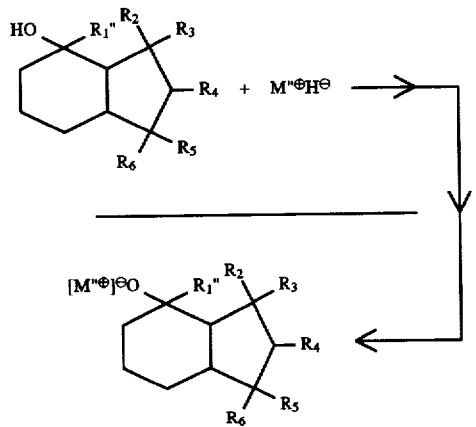

wherein $R_1''$ is hydrogen, methyl or ethyl and $R_2$, $R_3$, $R_4$, $R_5$ and $R_6$ are defined, supra. The resulting salt having the structure:

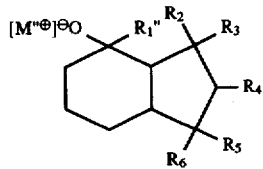

is then reacted with the etherifying reagent having the structure:

wherein $R_7$ and Y have been defined, supra, according to the reaction:

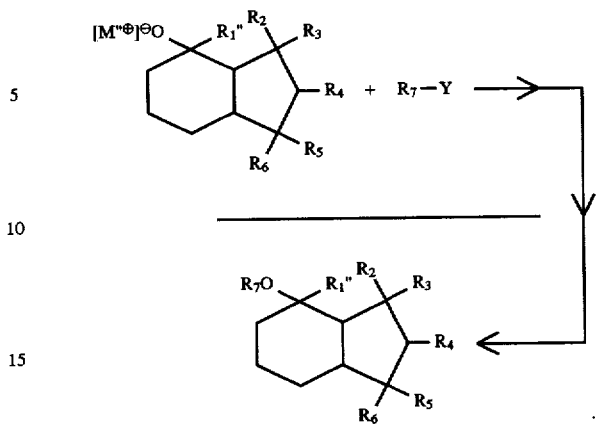

With respect to the Grignard reaction, the organometallic salt formed when the reagent:

is reacted with a ketone or mixture of ketones defined according to the structure:

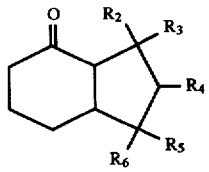

has the following structure:

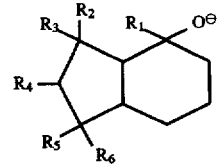

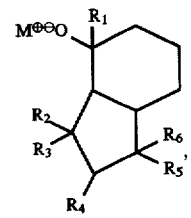

whereas when the Grignard reaction is carried out using the Grignard reagent having the structure:

the salt having the structure:

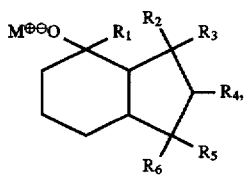

is formed. Both of the foregoing compounds are shown by the structure:

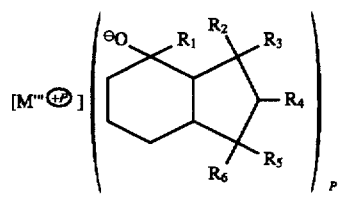

wherein M''', P, $R_1$, $R_2$, $R_3$, $R_4$, $R_5$ and $R_6$ have been defined, supra.

The Grignard reaction is carried out in the presence of an inert solvent such as tetrahydrofuran or diethyl ether as set forth, supra. The reaction temperature may vary between $-10°$ C. and $+10°$ C. for the formation of the salt, and the reaction temperature may vary between about 15° C. up to about 30° C. for the hydrolysis reaction. The mole ratio of ketone:Grignard reagent is preferably slightly greater than 1:1 in favor of the ketone (that is, where the ketone reactant is in excess). The concentration of Grignard reagent in solution (that is, in the inert solvent) may vary from about 0.5 up to about 1 mole per liter. In the hydrolysis reaction, other acidic medium may be used, for example, dilute acetic acid.

With respect to the etherification procedure, the mole ratio of alkali metal hydride:alcohol is preferably slightly greater than 1:1 in favor of the alkali metal hydride. Preferably the mole ratio of alkali metal hydride:alcohol is about 1.3:1. The reaction also takes place in the presence of an inert solvent such as tetrahydrofuran or diethyl ether, and the alkali metal hydride is used in solution wherein the solvent is the inert solvent, e.g., tetrahydrofuran. The reaction temperature for the formation of the alkali metal salt is in the range of from about 65°–75° C. The time of reaction is between about 3 hours and about 5 hours.

With respect to the reaction of the etherifying reagent with the resulting salt, the temperature of reaction is between about 75° C. and about 80° C. and the time of reaction is between about 5 and 15 hours. The reaction of the etherification reagent with the salt also takes place in the presence of an inert solvent, which is the same solvent as the one for the formation of the salt, e.g., tetrahydrofuran or diethyl ether. If an inert solvent such as diethyl ether is used when using the higher reaction temperatures, higher pressures must be employed; that is, super atmospheric pressures, e.g., 5–10 atmospheres. The reaction using the tetrahydrofuran solvent may take place at 1 atmosphere.

At the end of the reaction, the reaction mass is quenched with water and extracted with solvent, such as diethyl ether. The extract is stripped of solvent and distilled preferably by means of fractional distillation. The resulting fractions are bulked and utilized for their organoleptic properties.

The following table sets forth reaction products of our invention and their corresponding organoleptic properties:

TABLE I

| Structure of Reaction Product | Perfume Properties |
|---|---|
| The mixture of compounds defined according to the structure: ![structure] (a mixture of the compounds having the structures: [structures shown]) prepared according to Example I, distillation fractions 13–18. | An amber, cedarwood, fruity, bois ambrene, limlewood (fir), and green wood aroma with cedarwood and amber topnotes. |
| The mixture of compounds defined according to the structure: ![structure] (containing the compounds having the structures: [structure shown]) | A woody and amber aroma. |

TABLE I-continued

| Structure of Reaction Product | Perfume Properties |
|---|---|
| 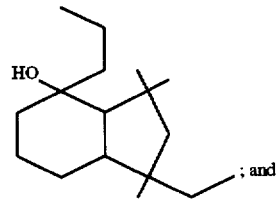 ; and 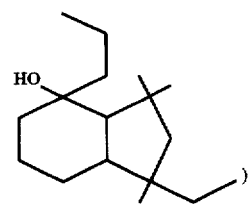 ) prepared according to the procedure of Example II, distillation fractions 12–15. | |
| The mixture of compounds having the structure: 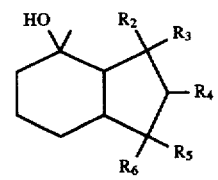 (containing the compounds having the structures: 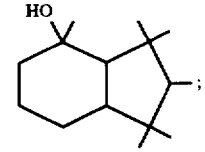 ; 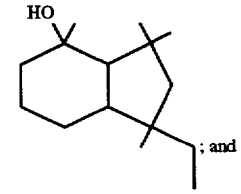 ; and 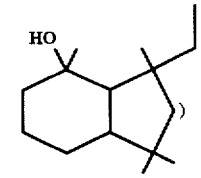 ) prepared according to Example III, bulked distillation fractions 15–23. | An amber, cassis, juniper, bois ambrene, limlewood (fir), fresh cut cedarwood, animalic, musky and camphoraceous aroma with woody, sandalwood, amber, musky and kephalis topnotes. |
| The mixture of compounds defined according to the structure: | A green, woody, balsamic, amber and |

TABLE I-continued

| Structure of Reaction Product | Perfume Properties |
|---|---|
| 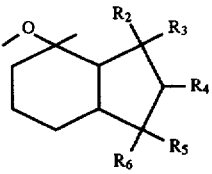 (containing the compounds having the structures: 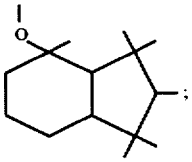 ; 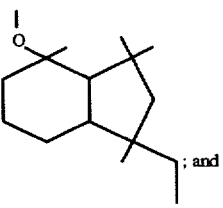 ; and 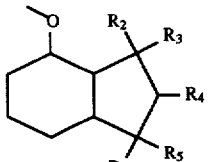 ) prepared according to the procedure of Example IV, bulked distillation fractions 8–14. | fruity aroma with green, woody, balsamic, amber and fruity topnotes. |
| The mixture of compounds defined according to the structure: 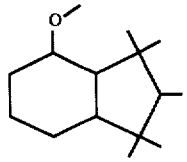 (containing the compounds having the structures: 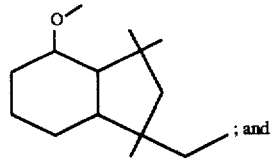 ; and | An intense, woody, jasmine, fatty and musky aroma with intense and long lasting woody, cedarwood, musky, balsamic, amber and fruity topnotes. |

TABLE I-continued

| Structure of Reaction Product | Perfume Properties |
| --- | --- |
| 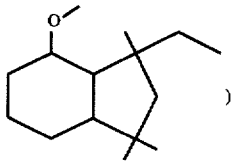 prepared according to the procedure of Example V, bulked distillation fractions 12–18. | |

At least one of the methyl substituted hexahydroindanols and alkyl ethers thereof of our invention prepared in accordance with the process of our invention and one or more auxiliary perfume ingredients including, for example, alcohols other than the methyl substituted hexahydroindanols and alkyl ethers thereof of our invention, aldehydes, ketones, terpenic hydrocarbons, nitriles, esters, lactones, ethers other than the methyl substituted hexahydroindanols and alkyl ethers thereof of our invention, natural essential oils and synthetic essential oils may be admixed so that the combined odors of the individual components produce a pleasant and desired fragrance, particularly and preferably in the piney and patchouli fragrance areas. Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute to their particular olfactory characteristics; however, the overall sensory effect of the perfume composition will be at least the sum total of the effects of each of the ingredients. Thus, at least one of the methyl substituted hexahydroindanols and alkyl ethers thereof of our invention prepared in accordance with the processes of our invention can be used to alter, modify or enhance the aroma characteristics of a perfume composition, for example, by utilizing or moderating the olfactory reaction contributed by another ingredient in the composition.

The amount of at least one of the methyl substituted hexahydroindanols and alkyl ethers thereof of our invention prepared in accordance with the processes of our invention which will be effective in perfume compositions as well as in perfumed articles (e.g., anionic, nonionic, cationic or zwitterionic detergents, soaps, fabric softener compositions and articles, and hair preparations) and colognes depends upon many factors including the other ingredients, their amounts and the effects which are desired. It has been found that perfume compositions containing as little as 0.01% of at least one of the methyl substituted hexahydroindanols and alkyl ethers thereof of our invention prepared in accordance with the processes of our invention or even less (e.g., 0.005%) can be used to impart a woody, amber, cedarwood, fresh cut cedarwood, fruity, bois ambrene, limlewood (fir), green, green wood, balsamic, cassis, juniper, animalic, camphoraceous, musky, jasmine and fatty aroma with woody, cedarwood, amber, fruity, sandalwood, musky, kephalis, green and balsamic topnotes to soaps, cosmetics, anionic, nonionic, cationic or zwitterionic detergents, fabric softener compositions, fabric softener articles, perfumed polymers and the like. The amount employed can range up to 70% of the fragrance components and will depend on considerations of cost, nature of the end product, the effect desired on the finished product and the particular fragrance sought.

One or more of the methyl substituted hexahydroindanols and alkyl ethers thereof of our invention prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders such as talcs, dusting powders, face powders, perfumed polymers and the like.

When used as (an) olfactory component(s), as little as 0.2% of one or more of the methyl substituted hexahydroindanols and alkyl ethers thereof of our invention prepared in accordance with the processes of our invention will suffice to impart an intense and long lasting, woody, amber, cedarwood, fresh cut cedarwood, fruity, bois ambrene limlewood (fir), green, green wood, balsamic, cassis, juniper, animalic, musky, camphoraceous, jasmine and fatty aroma with woody, cedarwood, amber, fruity, sandalwood, musky, kephalis, green and balsamic topnotes to patchouli, vetiver and pine formulations. Generally, no more than 6% of one or more of the methyl substituted hexahydroindanols and alkyl ethers thereof of our invention prepared in accordance with the processes of our invention based on the ultimate end product are required in the perfumed article composition. Accordingly, the range of the use of the methyl substituted hexahydroindanols and alkyl ethers thereof of our invention in a perfumed article may vary from about 0.2% up to about 6% by weight of the ultimate perfumed article.

In addition, the perfume compositions or fragrance compositions of our invention can contain a vehicle or carrier for one or more of the methyl substituted hexahydroindanols and alkyl ethers thereof of our invention prepared in accordance with the processes of our invention. The vehicle can be a liquid such as a non-toxic alcohol, e.g., ethyl alcohol; a non-toxic glycol, e.g., proplyene glycol, or the like. The carrier can also be an absorbent solid such as gum (e.g., gum arabic, xanthan gum or guar gum) or components for encapsulating the composition (such as gelatin as by coacervation or such as a urea-formaldehyde prepolymer when forming a urea-formaldehyde polymer wall around a liquid center).

It will thus be apparent that one or more of the methyl substituted hexahydroindanols and alkyl ethers thereof of our invention prepared in accordance with the processes of our invention can be utilized to alter, modify or enhance sensory properties, particularly organoleptic properties such as fragrances of a wide variety of consumable materials.

The following Examples I, II, III, IV and V illustrate methods of our invention used to manufacture the methyl substituted hexahydroindanols and alkyl ethers thereof of our invention. Examples VI, et seq., serve to illustrate the organoleptic utilities of the methyl substituted hexahydroindanols and alkyl ethers thereof of our invention.

All parts and percentages given herein are by weight unless otherwise specified.

EXAMPLE I

PREPARATION OF 4-ETHYL HEXAHYDRO METHYL SUBSTITUTED-4-INDANOL MIXTURE

Reaction

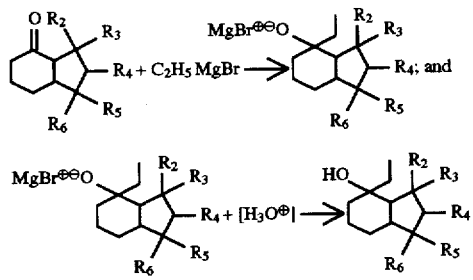

wherein $R_2$, $R_3$, $R_4$, $R_5$ and $R_6$ are defined, supra.

Into a 5 liter reaction vessel equipped with stirrer, thermometer, cooling coils, reflux condenser and heating mantle is placed a solution containing 7.2 moles of ethyl magnesium bromide in 2,400 ml of tetrahydrofuran.

The resulting solution is cooled to 0° C. Over a period of 1.5 hours, 816 grams (4 moles) of a mixture of compounds defined according to the structure:

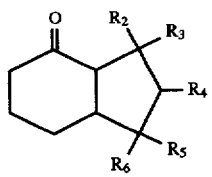

(mixture of the compounds having the structures:

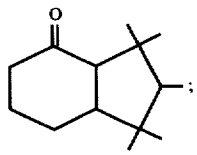

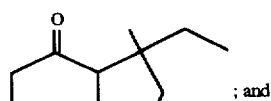

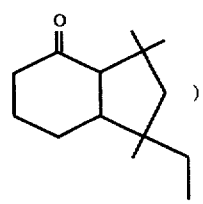

is added to the solution of ethyl magnesium bromide with stirring while maintaining the temperature of the reaction mass at 5° C. The reaction mass is warmed to room temperature (25° C.) and maintained at 25° C. with stirring for a period of 2.33 hours.

At the end of the 2.33 hour period, the mixture of compounds contained in the reaction mass is defined according to the structure:

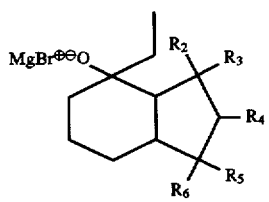

wherein in the mixture in each of the compounds $R_2$, $R_3$, $R_4$, $R_5$ and $R_6$ are defined, supra.

The resulting solution containing the organometallic salt is quenched by pouring same into a container containing:

(a) 3 liters 10% acetic acid;
(b) ice; and
(c) 1.5 liters toluene.

The organic phase is then separated from the aqueous phase. The organic phase is washed as follows:

(a) three 2 liter portions of saturated aqueous sodium bicarbonate solution; and then
(b) one 2 liter portion of saturated aqueous sodium chloride solution.

The resultant product is filtered through CELITE®/anhydrous sodium sulfate. The resulting filtrate (1,394 grams) is then fractionally distilled yielding the following distillation fractions:

| Fraction Number | Vapor Temperature (°C.) | Liquid Temperature (°C.) | Vacuum mm/Hg Pressure |
| --- | --- | --- | --- |
| 1 | 31/8 | 58/90 | 100/3.2 |
| 2 | 126 | 138 | 2.50 |
| 3 | 110 | 220 | 2.60 |

Fractions 2 and 3 are bulked and redistilled at 115° C., 2.55 mm/Hg to yield 20 fractions.

Fractions 13–18 are bulked. NMR, IR and mass spectral analysis confirm that the resulting product is a mixture of compounds defined according to the structure:

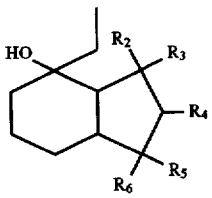

(containing the compounds having the structures:

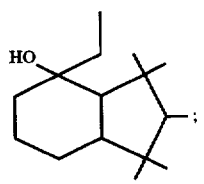

-continued

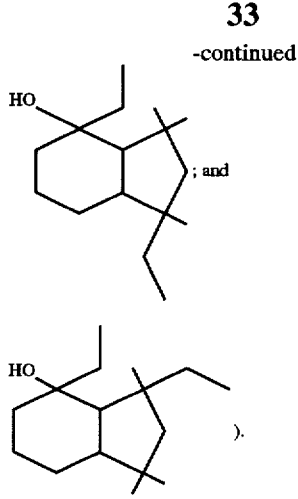
); and

EXAMPLE II

PREPARATION OF 4-n-PROPYL-HEXAHYDROMETHYL SUBSTITUTED-4-INDANOL MIXTURE

Reactions

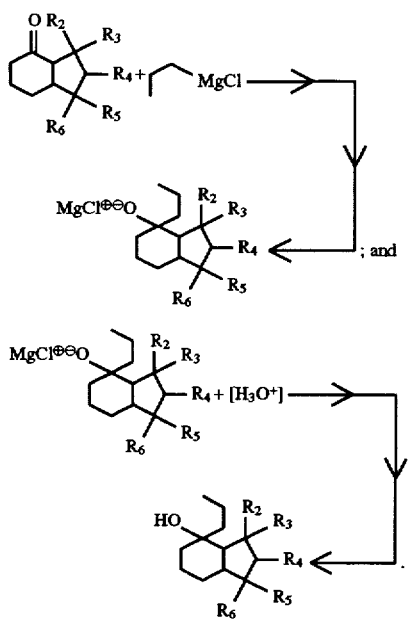

Into a 5 liter reaction vessel equipped with stirrer, thermometer, cooling coils, reflux condenser and heating mantle is placed a solution of 20 moles of n-propyl magnesium chloride in 3,200 ml of tetrahydrofuran. The n-propyl magnesium chloride solution is cooled to 0° C.

Over a period of 2.25 hours, the mixture of compounds defined according to the structure:

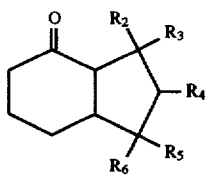

(mixture of the compounds having the structures:

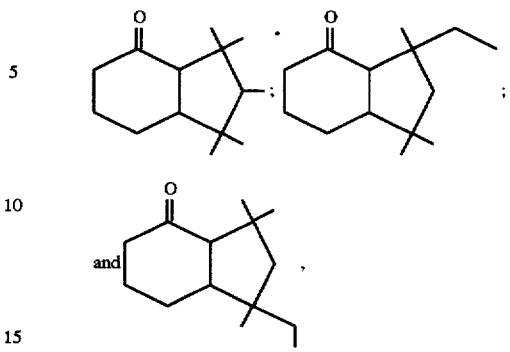

is added to the reaction mass while maintaining the reaction mass at 5° C.

At the end of the 2.25 hour period, the temperature of the reaction mass is permitted to rise to 24°–27° C.

At this point in time, the reaction mass contains a solution of a mixture of organometallic salts defined according to the structure:

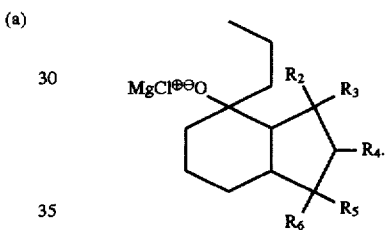

The resulting salt solution in tetrahydrofuran is quenched by pouring same into a mixture of ice, toluene and 3 liters of 10% aqueous acetic acid.

The resulting product now exists in two phases: an organic phase and an aqueous phase. The organic phase is separated from the aqueous phase and washed as follows:

(a) five 2 liter portions of saturated aqueous sodium bicarbonate; and (b) 2 liters of saturated aqueous sodium chloride.

The resulting product is filtered through CELITE®/anhydrous sodium sulfate and then distilled on a fractionation column yielding the following fractions:

| Fraction Number | Vapor Temperature (°C.) | Liquid Temperature (°C.) | Vacuum mm/Hg Pressure |
|---|---|---|---|
| 1 | 22/67 | 42/50 | 90/96 |
| 2 | 73 | 139 | 5.90 |
| 3 | 115 | 126 | 3.2 |
| 4 | 84 | 195 | 5.6 |

Fraction 3 is separated and refractionated on a fractional distillation column yielding twenty fractions. Fractions 12–15 are bulked. The resulting product is a mixture of compounds defined according to the structure:

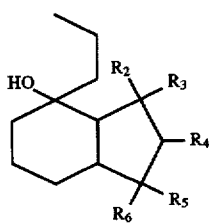

(a mixture of the compounds having the structures:

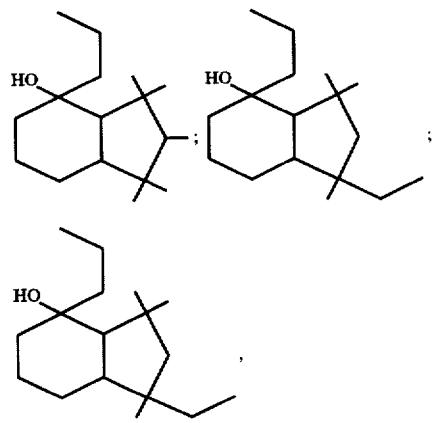

as confirmed by NMR, IR and mass spectral analyses.

EXAMPLE III

PREPARATION OF 4-METHYL-HEXAHYDRO-METHYL SUBSTITUTED-4-INDANOL

Reactions

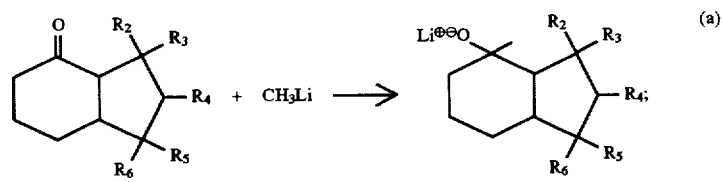

and

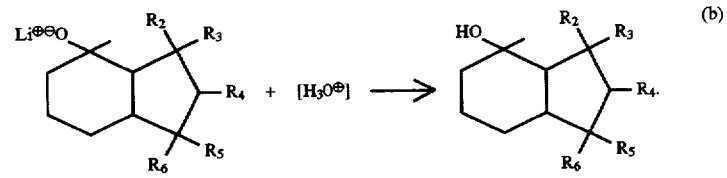

Into a 5 liter reaction vessel equipped with stirrer, thermometer, reflux condenser, heating mantle and cooling coils is placed a solution containing 2.24 moles methyl lithium in 600 ml of tetrahydrofuran. The contents of the reaction vessel is cooled to 0° C. Over a period of 1 hour, grams (1.6 moles) of the mixture of ketones defined according to the structure:

(a mixture of compounds having the structures:

and is added to the reaction mass while maintaining the reaction temperature at between −2° C. and 0° C. The reaction mass is then maintained at 0° C. with stirring for a period of 3 hours. At this point in time, the reaction mass contains a solution of the organometallic salt having the structure:

(a)

(b)

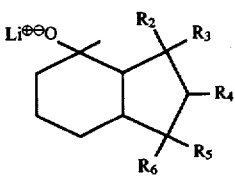

wherein in the mixture in each of the compounds $R_2$, $R_3$, $R_4$, $R_5$ and $R_6$ are as defined, supra The reaction mass is quenched with 1 liter of 4 molar aqueous hydrochloric acid. The reaction mass now exists in two phases: an organic phase and an aqueous phase. The organic phase is separated from the aqueous phase.

The organic phase is washed as follows:

(a) four 1 liter portions of saturated aqueous sodium bicarbonate;

(b) one 1 liter portion of water; and (c) one 1 liter portion of saturated aqueous sodium chloride.

The resulting product is then filtered through CELITE®/ anhydrous sodium sulfate. The resulting product is then fractionally distilled yielding the following fractions:

| Fraction Number | Vapor Temperature (°C.) | Liquid Temperature (°C.) | Vacuum mm/Kg Pressure |
|---|---|---|---|
| 1 | 33/72 | 75/120 | 42/1.66 |
| 2 | 90 | 114 | 1.45 |
| 3 | 84 | 150 | 1.58 |

Fractions 2 and 3 are bulked and redistilled yielding 30 fractions. Fractions 15–23 distilling at 88°–91° C. (vapor temperature) and a vacuum of 1.44–1.6 mm/Hg are bulked.

The bulked fractions consist of a mixture of compounds defined according to the structure:

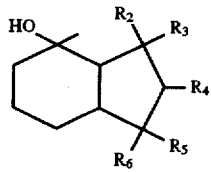

(the compounds having the structures:

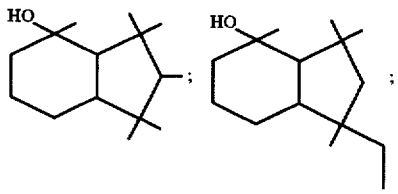

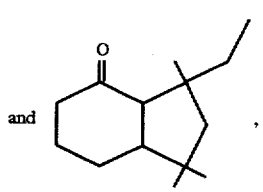

(wherein $R_2$, $R_3$, $R_4$, $R_5$ and $R_6$ are defined, supra) as confirmed by NMR, IR and mass spectral analyses.

EXAMPLE IV

PREPARATION OF HEXAHYDRO-4-METHOXY METHYL SUBSTITUTED INDANE MIXTURE

Reactions

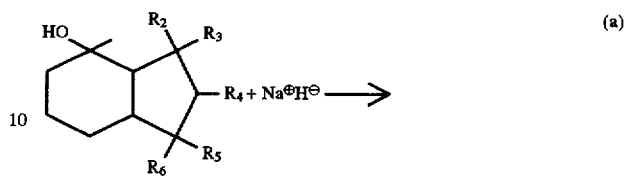
(a)

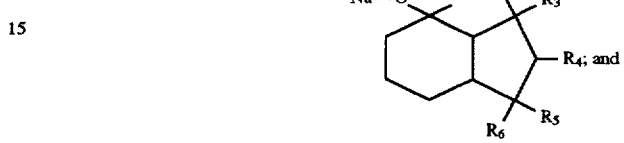

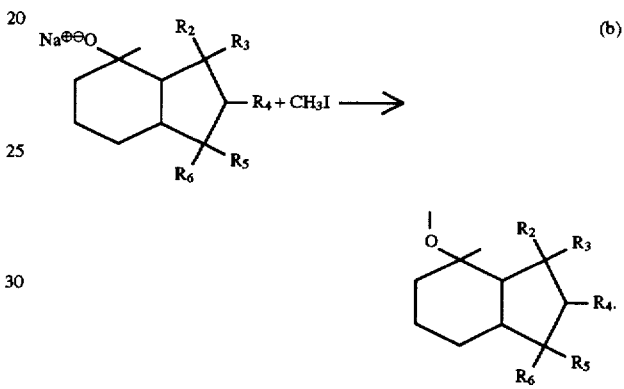
(b)

Into a 3 liter reaction vessel equipped with stirrer, thermometer, reflux condenser and heating mantle are placed 511 ml tetrahydrofuran and a solution of 156 grams of sodium hydride in 793.6 grams of tetrahydrofuran (3.9 moles). The resulting sodium hydride solution is heated to reflux (65° C.).

Over a period of 2 hours, while maintaining the reaction temperature at 65°–76° C. (reflux), 672 grams (3 moles) of the mixture of compounds defined according to the structures:

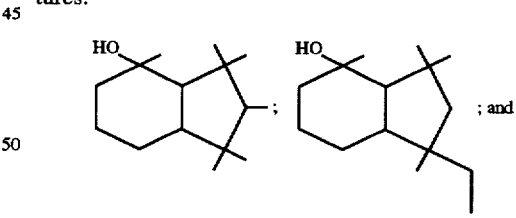

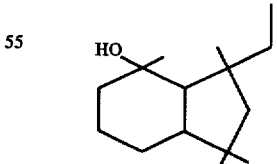

prepared according to Example III, bulked distillation fractions 15–23 is added to the reaction mass with stirring.

The reaction mass is then stirred at a temperature of 75°–76° C. for a period of 2.25 hours. At this point in time, the product in the reaction mass is the salt, in solution, having the structure:

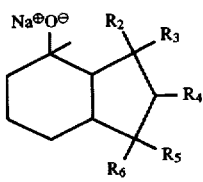

which structure represents a mixture, wherein in the mixture in each of the compounds, $R_2$, $R_3$, $R_4$, $R_5$ and $R_6$ are defined, supra.

Over a period of 2.5 hours while maintaining the reaction mass at 75°–78° C., 511 grams (3.6 moles) of methyl iodide is added to the reaction mass. The reaction mass is then stirred at a temperature of 78°–79° C. for a period of 6.5 hours.

At the end of the 6.5 hour period, the reaction mass is quenched with 1 liter of water. The product now exists in two phases: an organic phase and an aqueous phase. The organic phase is separated from the aqueous phase and washed with three 2 liter portions of water. The resulting product is then filtered through a CELITE®/anhydrous sodium sulfate filter bed.

The resulting product (89.22% yield) is then fractionally distilled yielding the following fractions:

| Fraction Number | Vapor Temperature (°C.) | Liquid Temperature (°C.) | Vacuum mm/Kg Pressure |
|---|---|---|---|
| 1 | 36/40 | 56/90 | 100/22 |
| 2 | 90 | 108 | 2.07 |
| 3 | 161 | 207 | 2.10 |

Fraction 2 is then fractionally distilled yielding 18 fractions. Fractions 8–14 are bulked and determined to be a mixture of compounds having the structures:

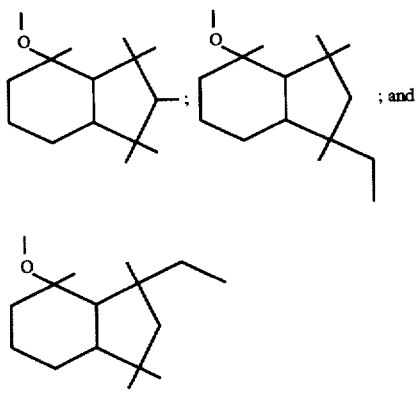

(as confirmed by NMR, IR and mass spectral analyses).

EXAMPLE V

PREPARATION OF SUBSTANTIALLY PURE HEXAHYDRO-4-METHOXY METHYL SUBSTITUTED INDANE MIXTURE

Reactions

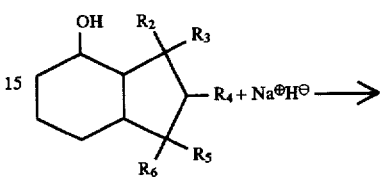 (a)

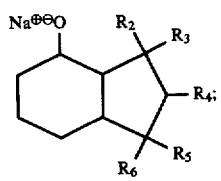

and

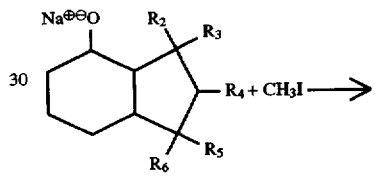 (b)

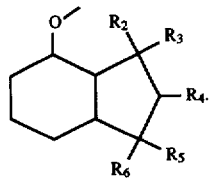

Into a 2 liter reaction flask equipped with stirrer, thermometer, reflux condenser and heating mantle are placed 737 ml of tetrahydrofuran and a solution containing 148 grams of sodium hydride in 371 ml of tetrahydrofuran. The resulting mixture is heated to reflux (66° C.) and while refluxing, over a period of 2 hours, 600 grams of the mixture of compounds having the structure:

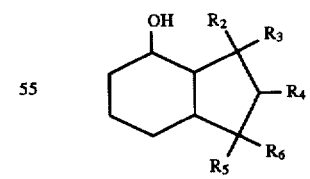

wherein in the mixture in each of the compounds $R_2$, $R_3$, $R_4$, $R_5$ and $R_6$ are defined, supra, is added to the reaction mass. The reaction mass is then maintained at 71°–72° C. for a period of 1 hour with stirring. At the end of the 1 hour period, the mixture of compounds defined according to the structure:

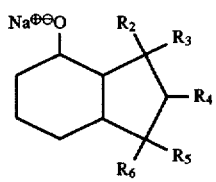

(wherein in the mixture in each of the compounds $R_2$, $R_3$, $R_4$, $R_5$ and $R_6$ are defined, supra) exists in solution.

While maintaining the reaction mass at 73° C., at reflux, 487 grams (3.43 moles) of methyl iodide is added to the reaction mass. The reaction mass is then cooled to room temperature and quenched with three 2 liter portions of water (pH=7.5). The resulting product is filtered through CELITE®/anhydrous sodium sulfate. The resulting product weighs 669 grams. The resulting product is fractionally distilled yielding the following fractions:

| Fraction Number | Vapor Temperature (°C.) | Liquid Temperature (°C.) | Vacuum mm/Kg Pressure |
| --- | --- | --- | --- |
| 1 | 22 | 86 | 2.28 |
| 2 | 87 | 110 | 0.972 |
| 3 | 160 | 193 | 0.650 |

Fraction 2 is redistilled yielding 20 fractions. Fractions 12–18, distilling at a vapor temperature of 87° C. and a vacuum of 0.96–0.98 mm/Hg, are bulked. The resulting bulked fraction is a substantially pure mixture of the compounds having the structures:

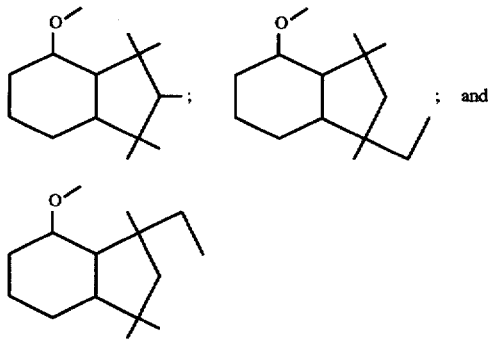

as determined by NMR, IR and mass spectral analyses.

EXAMPLE VI

The following Chypre formulations are prepared:

| Ingredients | Parts by Weight | | |
| --- | --- | --- | --- |
| | VI(A) | VI(B) | VI(C) |
| Musk ambrette | 40 | 40 | 40 |
| Musk ketone | 60 | 60 | 60 |
| Coumarin | 30 | 30 | 30 |
| Oil of bergamot | 150 | 150 | 150 |
| Oil of lemon | 100 | 100 | 100 |
| Methyl ionone | 50 | 50 | 50 |
| Hexyl cinnamic aldehyde | 100 | 100 | 100 |
| Hydroxycitronellal | 100 | 100 | 100 |
| Oil of lavender | 50 | 50 | 50 |
| Texas cedarwood oil | 85 | 85 | 85 |
| Virginia cedarwood oil | 30 | 30 | 30 |
| Oil of sandalwood (East Indies) | 40 | 40 | 40 |
| Isoeugenol | 20 | 20 | 20 |
| Eugenol | 10 | 10 | 10 |
| Benzyl acetate | 30 | 30 | 30 |
| β-phenyl ethyl alcohol | 40 | 40 | 40 |
| α-phenyl ethyl alcohol | 30 | 30 | 30 |
| Oakmoss absolute | 30 | 30 | 30 |
| Vetiver oil of Venezuela | 25 | 25 | 25 |
| The mixture of compounds defined according to the structure: | 25 | 0 | 0 |

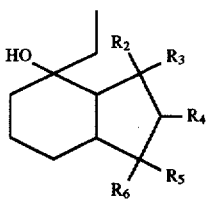

(a mixture of the compounds having the structures:

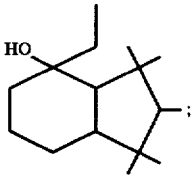

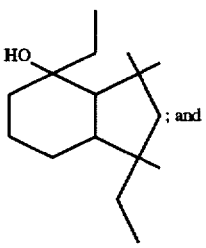

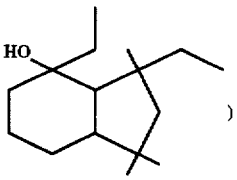

)

prepared according to Example I, distillation fractions 13–18.

| The mixture of compounds defined according to the structure: | 0 | 25 | 0 |
| --- | --- | --- | --- |

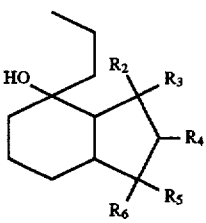

-continued

| | Parts by Weight | | |
|---|---|---|---|
| Ingredients | VI(A) | VI(B) | VI(C) |

(a mixture of compounds
having the structures:

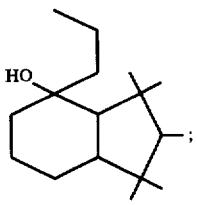

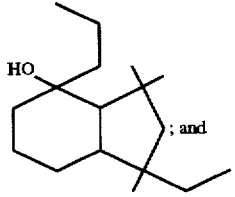; and

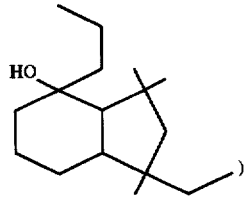)

prepared according to
Example II, bulked
distillation fractions 12–15.

| The mixture of compounds defined according to the structure: | 0 | 0 | 25 |

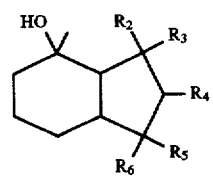

(a mixture of compounds
having the structures:

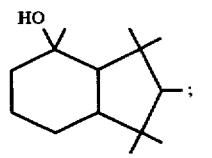;

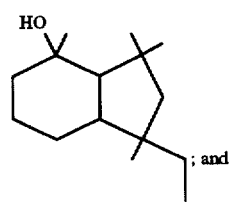; and

-continued

| | Parts by Weight | | |
|---|---|---|---|
| Ingredients | VI(A) | VI(B) | VI(C) |

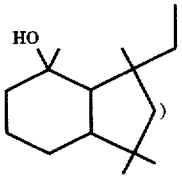)

prepared according to
Example III, bulked
distillation fractions 15–23.

The mixture of compounds defined according to the structure:

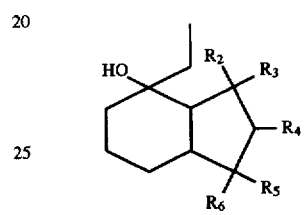

imparts to this Chypre formulation intense and long lasting amber, cedarwood, fruity, bois ambrene, limlewood (fir) and green wood undertones with cedarwood and amber topnotes. Accordingly, the formulation of Example VI(A) can be described as:

"a Chypre aroma having amber, cedarwood, fruity, bois ambrene, limlewood (fir) and green wood undertones with cedarwood and amber topnotes".

The mixture of compounds defined according to the structure

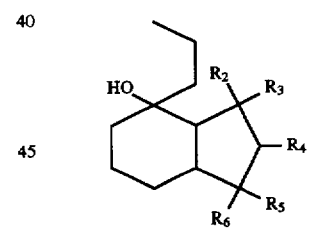

imparts to this Chypre formulation woody and amber undertones. Accordingly, the formulation of Example VI(B) is described as:

"a Chypre aroma with woody and amber undertones".

The mixture of compounds defined according to the structure:

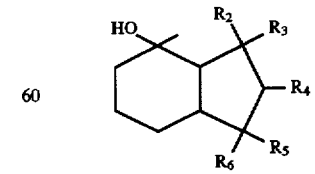

imparts to this Chypre formulation amber, cassis, juniper, bois ambrene, limlewood (fir), fresh cut cedarwood, animalic, musky and camphoraceous undertones with woody, sandalwood, amber, musky and kephalis topnotes. Accordingly, the perfume formulation of Example VI(C) is described as:

"a Chypre aroma with amber, cassis, juniper, bois ambrene, limlewood (fir), fresh cut cedarwood, animalic, musky and camphoraceous undertones with woody, sandalwood, amber, musky and kephalis topnotes".

EXAMPLE VII

PINE FRAGRANCES

The following pine fragrance formulations are produced:

| Ingredients | Parts by Weight | | |
|---|---|---|---|
| | VII (A) | VII (B) | VII (C) |
| Isobornyl acetate | 100 | 100 | 100 |
| Camphor | 10 | 10 | 10 |
| Terpineol | 25 | 25 | 25 |
| Fir balsam absolute (50% in diethyl phthalate) | 20 | 20 | 20 |
| Coumarin | 4 | 4 | 4 |
| Linalool | 30 | 30 | 30 |
| Fenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-trimethyl-1-cyclohexene-1-carboxaldehyde (LYRAL ®, trademark of International Flavors & Fragrances Inc.) | 12 | 12 | 12 |
| Maltol (1% in diethyl phthalate) | 5 | 5 | 5 |
| The mixture of compounds defined according to the structure: 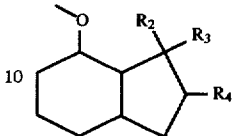 (a mixture of the compounds having the structures: 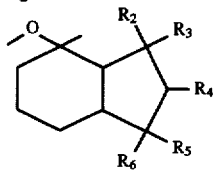 ; 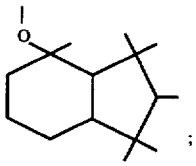 ; and 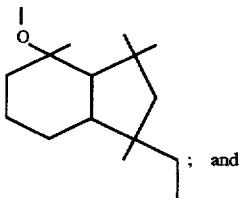 , 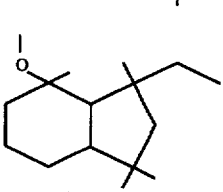 prepared according to Example IV, bulked distillation fractions 8–14. | 28 | 0 | 0 |
| The mixture of compounds defined according to the structure: 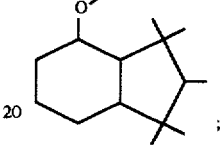 (a mixture of compounds having the structures: 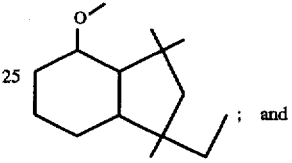 prepared according to Example V, bulked distillation fractions 12–18. | 0 | 28 | 0 |
| 50:50 (weight:weight) Mixture of compounds having the structure: 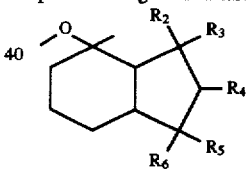 and mixture of compounds having the structure: 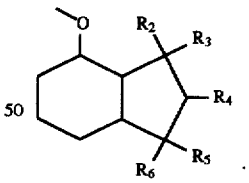 | 0 | 0 | 28 |

The mixture of compounds defined according to the structure:

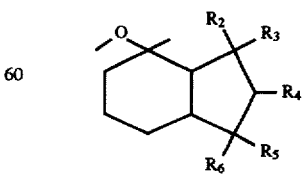

imparts to this pine fragrance green, woody, balsamic, amber and fruity undertones with green, woody, balsamic, amber and fruity topnotes. Accordingly, the pine fragrance of Example VII(A) can be described as:

"a pine aroma with green, woody, balsamic, amber and fruity undertones with green, woody, balsamic, amber and fruity topnotes".

The mixture of compounds defined according to the structure:

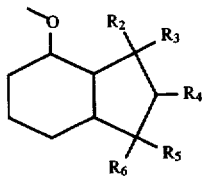

imparts to this pine fragrance formulation intense, woody, jasmine, fatty and musky undertones with intense and long lasting woody, cedarwood, musky, balsamic, amber and fruity topnotes. Accordingly, the pine fragrance of Example VII(B) is described as:

"a pine aroma with intense, woody, jasmine, fatty and musky undertones with intense and long lasting woody, cedarwood, musky, balsamic, amber and fruity topnotes".

The mixture of compounds defined according to the structures:

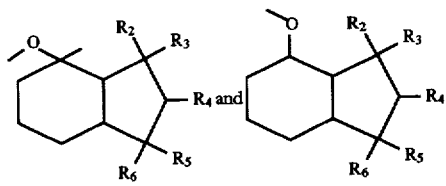

(50:50, weight:weight) imparts to this pine fragrance formulation long lasting and intense green, woody, balsamic, amber, fruity, jasmine, fatty and musky undertones with intense and long lasting woody, cedarwood, musky, balsamic, amber, fruity and green topnotes. Accordingly, the perfume formulation of Example VII(C) is described as:

"a pine aroma with green, woody, balsamic, amber, fruity, jasmine, fatty and musky undertones with intense and long lasting woody, cedarwood, musky, balsamic, amber, fruity and green topnotes".

EXAMPLE VIII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| The mixture of compounds defined according to the structure: | An amber, cedarwood, fruity, bois ambrene, limlewood (fir) and green wood aroma with cedarwood and amber topnotes. |
| prepared according to Example I, bulked distillation fractions 13–18. | |
| The mixture of compounds defined according to the structure: | A woody and amber aroma. |
| prepared according to Example II, bulked distillation fractions 12–15. | |
| The mixture of compounds defined according to the structure: | An amber, cassis, juniper, bois ambrene, limlewood (fir), fresh cut cedarwood, animalic, musky and camphoraceous aroma with woody, sandalwood, amber, musky and kephalis topnotes. |
| prepared according to Example III, bulked distillation fractions 15–23. | |
| The mixture of compounds defined according to the structure: | A green, woody, balsamic, amber and fruity aroma with green, woody, balsamic, amber and fruity topnotes. |
| prepared according to Example IV, bulked distillation fractions 8–14. | |
| The mixture of compounds defined according to the structure: | An intense, woody, jasmine, fatty and musky aroma with intense and long lasting woody, cedarwood, musky, balsamic, amber and fruity topnotes. |
| prepared according to Example V, bulked distillation fractions 12–18. | |
| The perfume composition of Example VI (A). | A Chypre aroma having amber, cedarwood, fruity, bois ambrene, limlewood (fir) and green wood undertones with cedarwood and amber topnotes. |
| The perfume composition of Example VI (B). | A Chypre aroma with woody and amber undertones |
| The perfume composition of Example VI (C). | A Chypre aroma with amber, cassis, juniper, bois ambrene, limlewood (fir), fresh cut cedarwood, animalic, musky and camphoraceous undertones with woody, sandalwood, amber, musky and kephalis topnotes. |
| The perfume composition of Example VII (A). | A pine aroma with green, woody, balsamic, amber and fruity undertones with green, woody, balsamic, |

TABLE II-continued

| Substance | Aroma Description |
|---|---|
| | amber and fruity topnotes. |
| The perfume composition of Example VII (B). | A pine aroma with intense, woody, jasmine, fatty and musky undertones with intense and long lasting woody, cedarwood, musky, balsamic, amber and fruity topnotes. |
| The perfume composition of Example VII (C). | A pine aroma with green, woody, balsamic, amber, fruity, jasmine, fatty and musky undertones with intense and long lasting woody, cedarwood, musky, balsamic, amber, fruity and green topnotes. |

EXAMPLE IX

PERFUMED LIQUID DETERGENTS

Concentrated liquid detergents (lysine salt of n-dodecylbenzene sulfonic acid as more specifically described in U.S. Pat No. 3,948,818 issued Apr. 6, 1976, incorporated by reference herein) with aroma nuances as set forth in Table II of Example VIII are prepared containing 0.10%, 0.15%, 0.20%, 0.25%, 0.30% and 0.35% of the substance set forth in Table II of Example VIII. They are prepared by adding and homogeneously mixing the appropriate quantity of substance set forth in Table II of Example VIII in the liquid detergent. The detergents all possess excellent aromas as set forth in Table II of Example VIII, the intensity increasing with greater concentrations of substance as set forth in Table II of Example VIII.

EXAMPLE X

PREPARATION OF COLOGNES AND HANDKERCHIEF PERFUMES

Compositions as set forth in Table II of Example VIII, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table II of Example VIII are imparted to the colognes and to the handkerchief perfumes at all levels indicated.

EXAMPLE XI

PREPARATION OF A SOAP COMPOSITION

100 Grams of soap chips (per sample) (IVORY® produced by the Procter & Gamble Company of Cincinnati, Ohio) are each mixed with 1 gram samples of substances as set forth in Table II of Example VIII until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example VIII.

EXAMPLE XII

PREPARATION OF SOLID DETERGENT COMPOSITIONS

Detergents are prepared using the following ingredients according to Example I of Canadian Patent No. 1,007,948 (incorporated by reference herein):

| Ingredient | Parts by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VIII. Each of the detergent samples has an excellent aroma as indicated in Table II of Example VIII.

EXAMPLE XIII

Utilizing the procedure of Example I of column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   1% of one of the perfume materials as set forth in Table II of Example VIII.

Fabric softening compositions prepared according to Example I at column 15 of U.S. Pat. No. 3,632,396 having aroma characteristics as set forth in Table II of Example VIII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example VIII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener, non-woven fabrics and these aroma characteristics are described in Table II of Example VIII.

EXAMPLE XIV

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid prepared by the Dow Corning Corporation | 0.10 |
| TWEEN ® 20 surfactant (prepared by ICI America Corporation) | 0.03 |
| One of the perfumery substances as set forth in Table II of Example VIII | 0.10 |

The perfuming substances as set forth in Table II of Example VIII add aroma characteristics as set forth in Table II of Example VIII which are rather intense and aesthetically pleasing to the users of the soft-feel, good-hold pump hair sprays.

EXAMPLE XV

CONDITIONING SHAMPOOS

Monamid CMA (prepared by the Mona Industries Company) (3.0 weight percent) is melted with 2.0 weight percent coconut fatty acid (prepared by the Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation.

The resulting material then mixed and cooled to 45° C., and 0.3 weight percent of perfuming substance as set forth in Table II of Example VIII is added to the mixture. The resulting mixture is cooled to 40° C. and blending is carried out for an additional 1 hour in each case. At the end of this blending period, the resulting material has a pleasant fragrance as indicated in Table II of Example VIII.

What is claimed:

1. A composition of matter comprising at least one methyl substituted hexahydroindanols and alkyl ethers thereof defined according to structure:

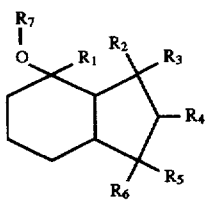

wherein $R_7$ represents hydrogen or $C_1$–$C_3$ alkyl; wherein $R_1$ represents methyl or ethyl; wherein $R_4$ represents methyl or hydrogen; and wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl.

2. The composition of claim 1 comprising a mixture consisting of compounds having the structures:

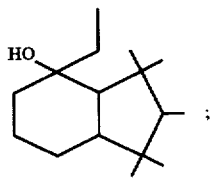

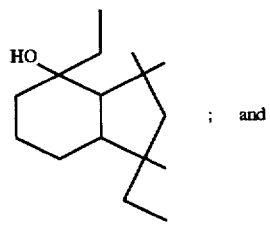

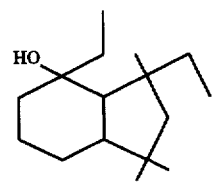

3. The composition of claim 1 comprising a mixture consisting of compounds having the structures:

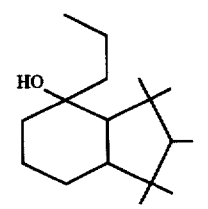

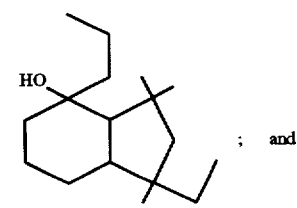

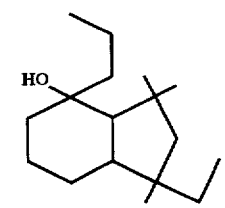

4. The composition of claim 1 comprising a mixture consisting of the compounds having the structures:

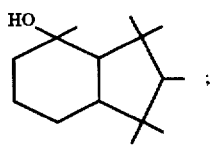

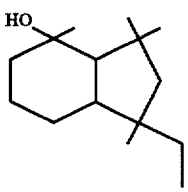

; and

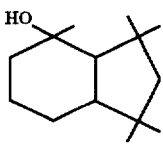

5. The composition of claim 1 comprising a mixture consisting of the compounds having the structures:

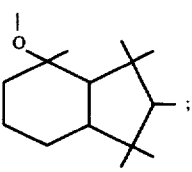

;

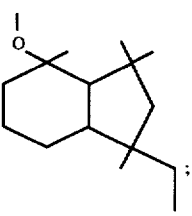

;

and

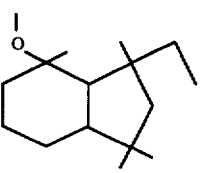

6. A substantially pure mixture of ethers consisting of compounds having the structures:

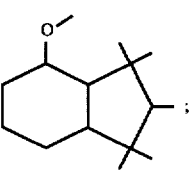

;

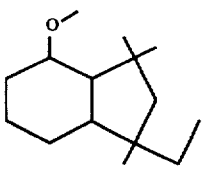

;

and

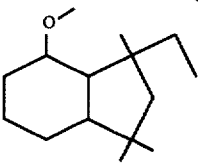

7. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 1.

8. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 2.

9. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 3.

10. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 4.

11. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 5.

12. A process for augmenting or enhancing the aroma of a perfume composition, cologne or perfumed article comprising the step of intimately admixing with a perfume base, a cologne base or a perfumed article base an aroma imparting, augmenting or enhancing quantity and concentration of the composition of matter defined according to claim 6.

13. A perfume composition comprising a perfume base and intimately admixed therewith an aroma augmenting, enhancing or imparting quantity and concentration of the composition of matter of claim 1.

14. A perfumed article comprising a perfumed article base and intimately admixed therewith an aroma augmenting, enhancing or imparting quantity and concentration of the composition of matter defined according to claim 1.

15. A cologne consisting of water, ethanol and an aroma imparting quantity of at least one methyl substituted hexahydroindanols and alkyl ethers thereof defined according to claim 1.

16. A perfume composition comprising a perfume base and intimately admixed therewith an aroma augmenting, enhancing or imparting quantity and concentration of the composition of matter of claim 6.

17. A perfumed article comprising a perfumed article base and intimately admixed therewith an aroma augmenting, enhancing or imparting quantity and concentration of the composition of matter of claim 6.

18. A cologne consisting of water, ethanol and an aroma imparting quantity and concentration of the composition defined according of claim 6.

19. An organometallic compound having the structure:

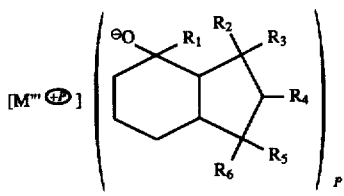

wherein $R_1$ represents ethyl or methyl; wherein $R_4$ represents methyl or hydrogen; and wherein $R_2$, $R_3$, $R_5$ and $R_6$ each represents methyl or ethyl with the provisos that:

(a) at least three of $R_2$, $R_3$, $R_5$ and $R_6$ represents methyl; and (b) when each of $R_2$, $R_3$, $R_5$ and $R_6$ is methyl then $R_4$ is methyl and wherein P represents the valence of M''' and is an integer selected from the group consisting of 1 and 2; and wherein M''' is selected from the group consisting of Li, MgX, Cd and Zn and wherein X is chloro, bromo or iodo.

20. The organometallic compound of claim 19 having the structure:

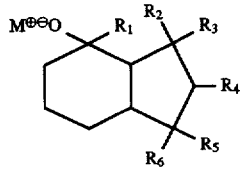

wherein M is selected from the group consisting of Li and MgX and wherein X is chloro, bromo or iodo.

21. The organometallic compound of claim 19 having the structure:

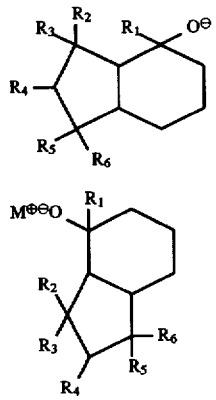

wherein M is selected from the group consisting of Cd and Zn.

22. An organometallic compound having the structure:

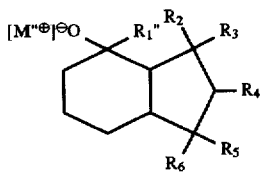

wherein $R_1''$ represents hydrogen, methyl or ethyl; wherein $R_4$ represents methyl or hydrogen; and wherein $R_2$, $R_3$, $R_5$ and $R_6$ each represents methyl or ethyl with the provisos that:

(a) at least three of $R_2$, $R_3$, $R_5$ and $R_6$ represents methyl; and (b) when each of $R_2$, $R_3$, $R_5$ and $R_6$ is methyl then $R_4$ is methyl and wherein M'' is alkali metal selected from the group consisting of sodium and potassium.

23. A process for preparing at least one indane derivative comprising the steps of carrying out the reactions:

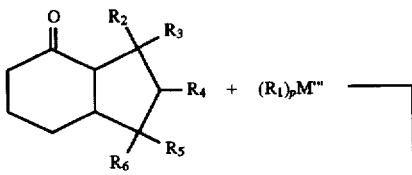

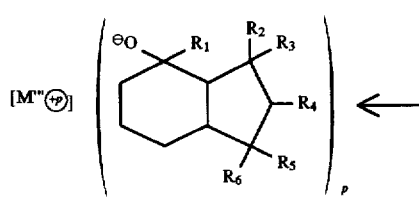

and

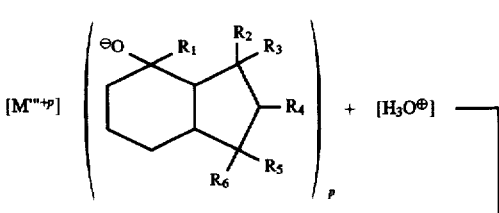

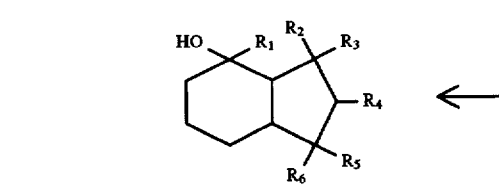

wherein $R_1$ is ethyl or methyl; wherein $R_4$ represents methyl or hydrogen; wherein $R_2$, $R_3$, $R_5$ and $R_6$ each represents methyl or ethyl with the provisos that:

(a) at least three of $R_2$, $R_3$, $R_5$ and $R_6$ represents methyl; and (b) when each of $R_2$, $R_3$, $R_5$ and $R_6$ is methyl then $R_4$ is methyl and wherein M''' is selected from the group consisting of Li, MgX, Cd and Zn; wherein X is chloro, bromo or iodo; and wherein P is the valence of M'''.

24. The process for preparing at least one indanyl ether derivative comprising the steps of carrying out the reactions:

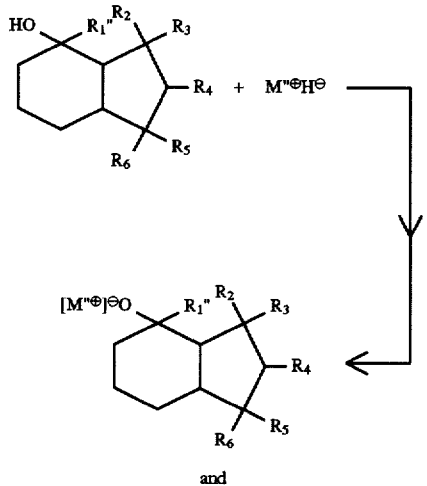

and

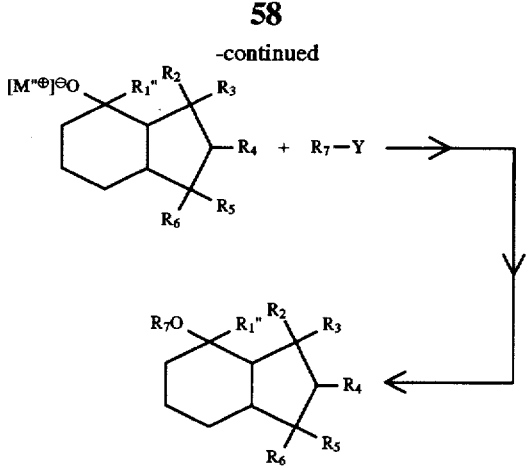

wherein $R_1''$ is hydrogen, ethyl or methyl; wherein $R_4$ represents methyl or hydrogen; wherein $R_2$, $R_3$, $R_5$ and $R_6$ each represents methyl or ethyl with the provisos that:

(a) at least three of $R_2$, $R_3$, $R_5$ and $R_6$ represents methyl; and (b) when each of $R_2$, $R_3$, $R_5$ and $R_6$ is methyl then $R_4$ is methyl and wherein M'' is alkali metal selected from the group consisting of sodium and potassium; wherein $R_7$ is $C_1$–$C_3$ alkyl; and wherein Y represents chloro, bromo or iodo.

* * * * *